United States Patent
Pratt et al.

(10) Patent No.: US 9,857,316 B2
(45) Date of Patent: Jan. 2, 2018

(54) METHODS AND APPARATUS FOR ELECTROMAGNETIC SIGNAL POLARIMETRY SENSING

(71) Applicant: University of Notre Dame du Lac, Notre Dame, IN (US)

(72) Inventors: Thomas G. Pratt, Niles, MI (US); Jeffrey George Mueller, South Bend, IN (US)

(73) Assignee: University of Notre Dame du Lac, South Bend, IN (US)

(*) Notice: Subject to any disclaimer, the term of this patent is extended or adjusted under 35 U.S.C. 154(b) by 783 days.

(21) Appl. No.: 13/837,937

(22) Filed: Mar. 15, 2013

(65) Prior Publication Data
US 2013/0332115 A1   Dec. 12, 2013

Related U.S. Application Data

(63) Continuation-in-part of application No. 13/349,968, filed on Jan. 13, 2012, now Pat. No. 9,037,414.

(51) Int. Cl.
| | |
|---|---|
| G01N 22/04 | (2006.01) |
| G01S 13/88 | (2006.01) |
| G01S 13/89 | (2006.01) |
| G01S 7/02  | (2006.01) |

(52) U.S. Cl.
CPC ............ G01N 22/04 (2013.01); G01S 7/024 (2013.01); G01S 13/885 (2013.01); G01S 13/89 (2013.01)

(58) Field of Classification Search
CPC ...... G01S 7/024; G01S 7/282; G01S 13/0209; G01S 13/885; G01S 13/89; G01S 13/36; G01S 7/38

USPC .............. 702/2; 342/22; 356/73.1; 324/326; 455/73, 118, 190.1
See application file for complete search history.

(56) References Cited

U.S. PATENT DOCUMENTS

| | | | |
|---|---|---|---|
| 5,557,277 A * | 9/1996 | Tricoles ................. | G01S 13/36 324/326 |
| 6,501,414 B2 * | 12/2002 | Arndt ..................... | F41H 11/12 342/194 |
| 6,850,318 B1 * | 2/2005 | Ito ...................... | G01M 11/3181 356/73.1 |

(Continued)

FOREIGN PATENT DOCUMENTS

JP          2003294580 A    * 10/2003

OTHER PUBLICATIONS

Zhang, Lamei; Zhang, Junping; Zou, Bin; Zhang, Ye; Comparison of Methods for Target Detection and Applications Using Polarimeteric SAR Image; 2008; Piers Online; vol. 4; No. 1; 140-145.*

*Primary Examiner* — Gregory J Toatley
*Assistant Examiner* — Terence Stifter, Jr.
(74) *Attorney, Agent, or Firm* — Greenberg Traurig, LLP

(57) ABSTRACT

A system and method of identifying changes utilizing radio frequency polarization includes receiving a reflected and/or transmitted polarized radio frequency signal at a receiver, filtering, amplifying and conditioning the received signal, converting the received signal from an analog format to a digital format, processing the digital signal to elicit a polarization mode dispersion feature of the received signal, and comparing the polarization mode dispersion features to a known calibration to detect a change in a characteristic of the target object.

13 Claims, 22 Drawing Sheets

(56) References Cited

U.S. PATENT DOCUMENTS

| | | | |
|---|---|---|---|
| 7,024,058 B2* | 4/2006 | Han | G02B 6/4215 385/11 |
| 8,417,192 B2* | 4/2013 | Brady | H04B 1/403 455/118 |
| 8,553,804 B2* | 10/2013 | Siwiak | H01Q 21/24 375/299 |
| 2002/0159334 A1* | 10/2002 | Caulfield | G01N 29/348 367/87 |
| 2005/0052638 A1* | 3/2005 | Ozeki | G01M 11/336 356/73.1 |
| 2007/0143036 A1* | 6/2007 | Stratis | G01N 23/00 702/28 |
| 2008/0129594 A1* | 6/2008 | Pera | H01Q 9/0435 342/361 |
| 2008/0218754 A1* | 9/2008 | Fest | F42C 13/023 356/369 |
| 2009/0190930 A1* | 7/2009 | Von Der Weid | H04B 10/2569 398/81 |
| 2009/0224964 A1* | 9/2009 | Raney | G01S 7/026 342/25 F |
| 2010/0003034 A1* | 1/2010 | Pratt | H04L 27/38 398/152 |
| 2010/0286152 A1* | 11/2010 | Bernasconi | C07D 211/34 514/249 |
| 2011/0205121 A1* | 8/2011 | Hochdorf | G01S 7/025 342/375 |
| 2012/0197641 A1* | 8/2012 | Akechi | G10L 15/08 704/236 |
| 2012/0236954 A1* | 9/2012 | Siwiak | H01Q 21/24 375/267 |
| 2013/0016418 A1* | 1/2013 | Chen | G02F 1/0123 359/279 |

* cited by examiner (a) 100Hz time domain (b) 100Hz frequency domain (a) 100Hz tuning fork time domain (b) 100Hz tuning fork frequency domain (a) rotating fan time domain (b) rotating fan frequency domain (a) nc-nc-nc-nc (b) c-nc-nc-nc (c) c-nc-nc-nc (d) c-nc-c-nc

METHODS AND APPARATUS FOR ELECTROMAGNETIC SIGNAL POLARIMETRY SENSING

CROSS REFERENCE TO RELATED APPLICATION

This application is a continuation-in-part application claiming priority to U.S. Ser. No. 13/349,968, now U.S. Pat. No. 9,037,414, filed Jan. 13, 2012, entitled "Methods and Apparatus for Radio Frequency Polarimetry Sensing", which is a non-provisional application claiming priority from U.S. Provisional Application Ser. No. 61/461,220, filed Jan. 14, 2011, entitled "Method and Apparatus for Soil Moisture Sensing," and U.S. Provisional Application Ser. No. 61/520,321, filed Jun. 8, 2011, entitled "Method and Apparatus for Soil Moisture Sensing," each of which are incorporated herein by reference in their entirety.

FIELD OF THE DISCLOSURE

The present description relates generally to electromagnetic signal sensing and more to methods and apparatus for electromagnetic polarimetry sensing.

BACKGROUND OF RELATED ART

Estimation of spatial and/or temporal variation in soil moisture is typically an important parameter in a number of applications ranging from efficiency of agricultural practices, to estimation of recharge to groundwater systems for modeling studies, to estimation of slope stabilities following precipitation, to monitoring the impact of mining operations. Such variation can be related to a number of interacting processes including heterogeneity of the sediments, spatial variation in recharge (related to spatial variation in precipitation, leaks in surface or buried pipelines, and vegetation), and spatial variation in evapotranspiration. Measurement of soil moisture is therefore an important challenge in a number of modeling and field optimization processes; a challenge which has attracted attention from the early days of technical research on the vadose zone to a plethora of journal articles focused on this soil property.

A number of methods have been developed to measure soil moisture either locally (e.g., at the meter scale or smaller) through direct or indirect measures on local sediments or at larger scales (10's of meters to watershed scale) through remote imaging. Briefly, local measures have been based predominantly on capacitance or resistance measures in soils, including time domain reflectometry (TDR), frequency domain reflectometry (FDR), and soil block measurements. To a lesser degree, soil tensiometers have been used to measure pore water pressure and this pressure has, through calibration of the pressure-moisture relationship, been related to soil moisture. These tools provide for measuring soil moisture at short time intervals with a support volume of the measurement on the order of the probe (e.g., soil blocks) to several multiples of the size of the probe (e.g., TDR and FDR) used in the measurement. As such, relatively precise measurement can be made, but field scale characterization of the spatial distribution of soil moisture would require a large number of probes.

In contrast, a number of imaging methods have been applied to measurement of the spatial distribution of soil moisture at scales ranging from agricultural fields to watersheds. Principal among these in the recent literature have been satellite imagery, thermal inertia methods, and assimilation of microwave signals. These methods have generally provided the ability to monitor the spatial distribution of soil moisture, but are limited spatially and temporally to locations where remotely sensed images are available (particularly for the satellite and temperature methods). Further, the spatial resolution is typically constrained by available storage/pixel dimensions.

Comparison of these two ranges of instruments (local versus large-scale) provides insight into a portion of the difficulty in integrating data over multiple scales of characterization with modeling efforts. Hence, the potential of remote measurement of soil moisture using available WLAN signals provides multiple advantages, including extremely low cost measurement with almost ubiquitous coverage in populated regions. Further, in light of the discussion above, WLAN networks also provide the promise of providing estimates of soil moisture over different averaging areas (averaging volumes) through judicious selection of beacon and receiver locations.

To date, radio frequency (RF) characterization of soil moisture has largely been associated with large-area characterizations using aerial reconnaissance and/or satellite observations. These approaches are constrained by limited earth coverage, low revisit times, and high cost, and do not offer flexibility to achieve customized monitoring architectures for smaller-scale applications. As one illustration, the Soil Moisture Active Passive (SMAP) Mission sensor estimates soil moisture at resolutions of 10 km with revisit intervals of 2 to 3 days. Such spatial and temporal resolutions are not well suited to address soil-moisture monitoring in low-cost field-scale applications requiring high revisit rates. Some experimentation has been performed using either active or passive ground-based RF systems. Active ground-based systems, mainly SAR systems, have been used for radar imaging of terrain and other applications including interferometric monitoring of large man-made structures. Most of the experimental systems described in literature are active systems with a Vector Network Analyzer (VNA) to perform a stepped frequency construction of a wide-band signal for high range resolution. Among the ground-based passive systems, a microwave radiometer has been used to infer soil moisture from polarization component magnitudes using non-coherent detection of ambient reflected microwaves over small areas for assimilation into precipitation models. A different passive ground based sensing approach employs an in-situ GPS receiver for near surface soil measurements. This sensing method exploits signals from the GPS constellation and measures SNR variations induced by satellite motion to infer soil moisture levels through subsequent model simulation. The technique reportedly offers resolutions on the order of 300 square meters, but the technique requires an in-situ receiver, relies on approximately 45 minutes of satellite motion to generate a useful output, assumes a single dominant multipath component and knowledge of various environmental parameters, and suffers from a relative lack of control over the transmitter/receiver geometry and corresponding sensing resolution.

The goal of known irrigation management techniques is to achieve an optimum water supply for crop productivity. Escalating worldwide water shortages and irrigation costs have resulted in an increasing emphasis on developing irrigation techniques that minimize water use while maintaining productivity (i.e. maximize water use efficiency). Irrigation scheduling techniques that are based on plant or soil water status can help achieve this goal. The advantage of soil moisture measurements over plant water status is that soil moisture measurements can be used to determine the amount of water that needs to be applied, while plant measurements merely indicate when water is needed, but not how much. In addition, soil moisture measurements can be easily integrated into automated systems. Conventional soil moisture monitoring techniques such as dielectric or resistance measurements in soils can be unwieldy in field-scale applications due to the need for contact with the soil and the large number of sensors required for suitable coverage.

Remote sensing approaches have advantages because of their capacity to integrate over large areas. Technologies such as aerial reconnaissance and/or satellite observations are widely used for large-area characterizations. However, these approaches are oftentimes constrained by limited earth coverage, low revisit times, low resolution, high cost, and do not offer flexibility to achieve customized monitoring for variable-scale applications.

DETAILED DESCRIPTION

Figure 1:
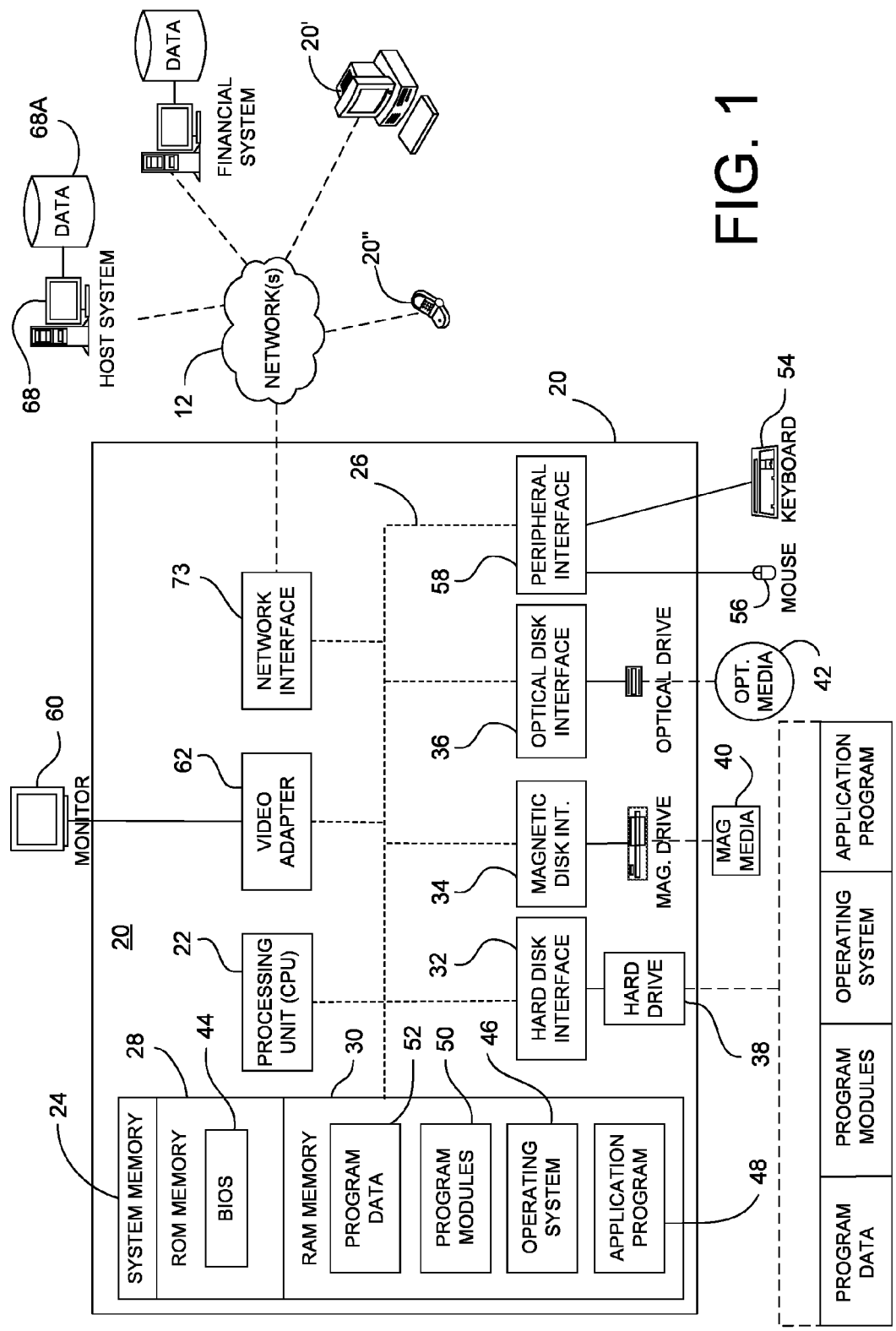
FIG. 1 illustrates in block diagram form components of an example, computer environment suitable for implementing the example methods and apparatus for radio frequency polarimetry sensing.

The following description of example methods and apparatus is not intended to limit the scope of the description to the precise form or forms detailed herein. Instead the following description is intended to be illustrative so that others may follow its teachings.

In contrast to the aforementioned remote ground-based techniques, the present disclosure describes a passive, coherent polarimetric soil moisture sensing concept. The example approach is designed to detect changes in bistatic scattering behavior from upper layers of the ground between local WLAN access points and the sensor. The method represents a highly portable, flexible, low-cost method that also provides some control over resolution scales via the antenna characteristics and deployment geometry between the transmitter, the receiver, and the ground to be monitored. Once installed, the system provides a low-cost continuous automated monitoring capability with easy access to data products. The disclosed approach may provide an advantage over the conventional satellite sensors exist in term of cost, cell resolution, revisit rates, persistence, ease of data retrieval, accuracy, ease of installation, and/or system portability.

There is a great need for remote sensing techniques as disclosed. For example, in an agricultural application, the present disclosure can provide scalable, low-cost, continuous monitoring of soil moisture. In particular, the present disclosure can enable improved irrigation practices to optimize crop growth and increase water use efficiency. For instance, a soil moisture sensing technology constructed in accordance with the teachings of the present disclosure operates by measuring polarimetric properties of bistatic clutter returns from the ground between a radio frequency (RF) transmitter and the receiver/sensor to detect changes in the reflected radio signal induced by changing soil moisture levels.

For instance in one example, a soil moisture sensor is capable of detecting and quantifying soil moisture under agricultural conditions. Additionally, the example is capable of identifying "drought triggers" by examining changes in the RF signal related to crop growth and physiology. Finally, the example soil moisture sensor technology may be utilized to replace relatively expensive instrumentation typically used for current methods.

To accomplish at least some of these features, the present disclosure may be utilized in various fields including, for example, in agricultural environments to detect, based upon RF-based polarimetry, changes in soil moisture in fallow fields and/or fields with crops. The sensors may be calibrated to obtain quantitative soil moisture estimates. At the same time crop growth and physiology can be monitored to correlate the measurements to the polarimetric measurements. The present example may also be utilized to determine the soil moisture profile versus depth by leveraging responses from different transmit frequencies, where lower frequencies provide increased penetration depths. The present RF polarimentric technology can thus impact horticultural and agricultural production.

With reference to the figures, the following discloses various example systems and methods for RF polarimetric sensing including, for instance, soil moisture detection. To this end, FIG. 1 illustrates a processing device 20", illustrated in the exemplary form of a mobile communication device, a processing device 20', illustrated in the exemplary form of a computer system, and a processing device 20 illustrated in schematic form, such as for example, a home computer, each of which may be provided with executable instructions to, for example, provide a means for a customer, e.g., an end user, representative, consumer, etc., to interact with the device 20 and/or to access a host system server 68. Generally, the computer executable instructions reside in program modules which may include routines, programs, objects, components, data structures, etc. that perform particular tasks or implement particular abstract data types. Accordingly, those of ordinary skill in the art will appreciate that the processing devices 20, 20', 20" illustrated in FIG. 1 may be embodied in any device having the ability to execute instructions such as, by way of example, an appliance, a personal computer, mainframe computer, personal-digital assistant ("PDA"), cellular telephone, tablet, ereader, or the like. Furthermore, while described and illustrated in the context of a single processing device 20, 20', 20" those of ordinary skill in the art will also appreciate that the various tasks described hereinafter may be practiced in a distributed environment having multiple processing devices linked via a local and/or wide-area network whereby the executable instructions may be associated with and/or executed by one or more of multiple processing devices. Still further, while described and illustrated in the context of a networked system, it will be understood that various portions of the present disclosure may be integrated into a single stand-alone environment.

For performing the various tasks in accordance with the executable instructions, the example processing device 20 includes a processing unit 22 and a system memory 24 which may be linked via a bus 26. Without limitation, the bus 26 may be a memory bus, a peripheral bus, and/or a local bus using any of a variety of bus architectures. As needed for any particular purpose, the system memory 24 may include read only memory (ROM) 28 and/or random access memory (RAM) 30. Additional memory devices may also be made accessible to the processing device 20 by means of, for example, a hard disk drive interface 32, a magnetic disk drive interface 34, and/or an optical disk drive interface 36. As will be understood, these devices, which would be linked to the system bus 26, respectively allow for reading from and writing to a hard disk 38, reading from or writing to a removable magnetic disk 40, and for reading from or writing to a removable optical disk 42, such as a CD/DVD ROM or other optical media. The drive interfaces and their associated computer-readable media allow for the nonvolatile storage of computer readable instructions, data structures, program modules and other data for the processing device 20. Those of ordinary skill in the art will further appreciate that other types of non-transitory computer readable media that can store data and/or instructions may be used for this same purpose. Examples of such media devices include, but are not limited to, magnetic cassettes, flash memory cards, digital videodisks, Bernoulli cartridges, random access memories, nano-drives, memory sticks, and other read/write and/or read-only memories.

A number of program modules may be stored in one or more of the memory/media devices. For example, a basic input/output system (BIOS) 44, containing the basic routines that help to transfer information between elements within the processing device 20, such as during start-up, may be stored in ROM 28. Similarly, the RAM 30, hard drive 38, and/or peripheral memory devices may be used to store computer executable instructions comprising an operating system 46, one or more applications programs 48 (such as a Web browser), other program modules 50, and/or program data 52. Still further, computer-executable instructions may be downloaded to one or more of the computing devices as needed, for example via a network connection.

To allow a user to enter commands and information into the processing device 20, input devices such as a keyboard 54 and/or a pointing device 56 are provided. While not illustrated, other input devices may include a microphone, a joystick, a game pad, a scanner, a camera, a touchpad, touch screen, motion sensor, etc. These and other input devices would typically be connected to the processing unit 22 by means of an interface 58 which, in turn, would be coupled to the bus 26. Input devices may be connected to the processor 22 using interfaces such as, for example, a parallel port, game port, firewire, or a universal serial bus (USB). To view information from the processing device 20, a monitor 60 or other type of display device may also be connected to the bus 26 via an interface, such as a video adapter 62. In addition to the monitor 60, the processing device 20 may also include other peripheral output devices, not shown, such as, for example, speakers, cameras, printers, or other suitable device.

As noted, the processing device 20 may also utilize logical connections to one or more remote processing devices, such as the host system server 68 having associated data repository 68A. In this example, the server 68 may act as a processor as described herein. In this regard, while the host system server 68 has been illustrated in the exemplary form of a computer, it will be appreciated that the host system server 68 may, like processing device 20, be any type of device having processing capabilities. Again, it will be appreciated that the host system server 68 need not be implemented as a single device but may be implemented in a manner such that the tasks performed by the host system server 68 are distributed amongst a plurality of processing devices/databases located at different geographical locations and linked through a communication network. Additionally, the host system server 68 may have logical connections to other third party systems via a network 12, such as, for example, the Internet, LAN, MAN, WAN, cellular network, cloud network, enterprise network, virtual private network, wired and/or wireless network, or other suitable network, and via such connections, will be associated with data repositories that are associated with such other third party systems. Such third party systems may include, without limitation, systems of banking, credit, or other financial institutions, systems of third party providers of goods and/or services (e.g., inventory), systems of shipping/delivery companies, etc.

For performing tasks as needed, the host system server 68 may include many or all of the elements described above relative to the processing device 20. Communications between the processing device 20 and the host system server 68 may be exchanged via a further processing device, such as a network router (not shown), that is responsible for network routing. Communications with the network router may be performed via a network interface component 73. Thus, within such a networked environment, e.g., the Internet, World Wide Web, LAN, cloud, or other like type of wired or wireless network, it will be appreciated that program modules depicted relative to the processing device 20, or portions thereof, may be stored in the non-transitory memory storage device(s) of the host system server 68.

Figure 2:
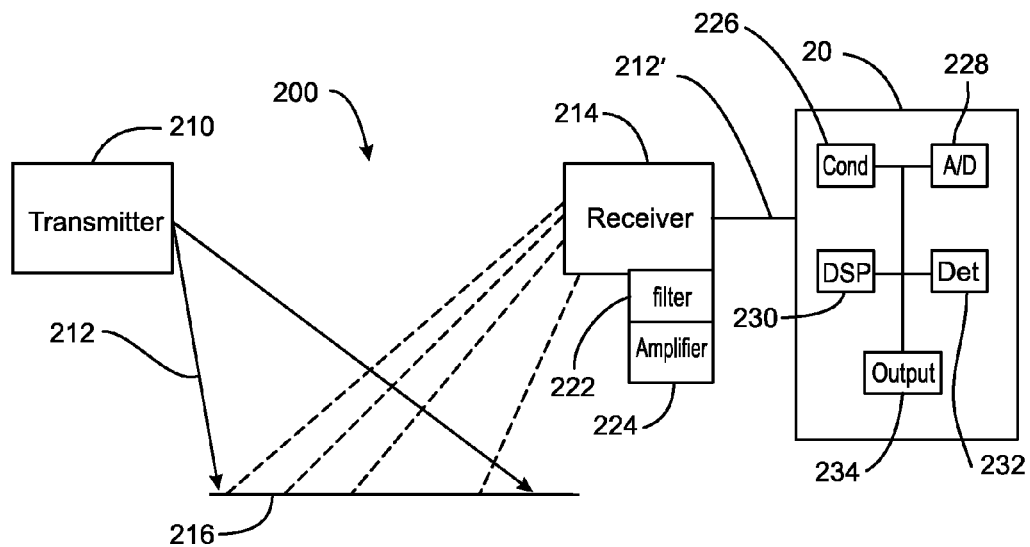
FIG. 2 illustrates an example radio frequency polarimetry sensing system in accordance with the teachings of the present disclosure.

Referring now to FIG. 2, an example sensor system 200 configuration is illustrated. In the illustrated example, a transmitter 210 is configured to actively transmit an electromagnetic signal, such as for example, a radio frequency signal 212. The electromagnetic signal 212 may be any type of electromagnetic signal including at least one of a radio frequency signal, a microwave signal, an infrared signal, a visible light signal, an ultraviolet radiation signal, an X-ray signal, or a gamma ray signal. A receiver 214 is positioned to receive the transmitted signal 212 reflected by a target object 216. The receiver 214, in turn may be communicatively coupled to the processing device 20 to perform the RF polarimetric processing. In one example, the receiver 214 relies on the propagation of beacon transmissions from the transmitter 210, which in this example is a WLAN access point. The example access point transmits a beacon pulse approximately every 100 ms. The transmit signal 212 energy is reflected by the target object 216, such as for example, the ground (including sublayers) residing in the local environment. The reflected signals 212 will generally have different path delays and will exhibit different scattering characteristics in amplitude and in polarimetric response that will depend upon the reflecting medium. The receiver 214 collects energy that is reflected by the object 216 to be characterized. Other signals, such as line-of sight (LOS) components from the transmitter, and also undesired multi-path reflections and/or scattering from nearby objects may also be simultaneously present at the receiver. LOS signals are typically unreflected, although in the instance where the target 216 is transmissive, the LOS signals may be impacted. Thus, the polarization sate of these signals are usually not affected like the signals that are reflected off the target 216. Accordingly, in one example the polarization state of these LOS signals can be compare with the polarization state of signals reflected off the target 216. As used in this application it should be understood the word "reflected" is being used in a broad sense to include instances where electromagnetic energy may be scattered, or transmitted through or off of an object.

While the present example is disclosed and illustrated as a bistatic system, it will be appreciated that the system 200 may be configured as a monostatic system as desired. Still further, the system 200 need not rely upon a reflection of the signal 212 off of the target object 216, but rather may additionally or alternatively utilize transmission of the signal 212 through the object 216 such as, for example, fog or other hydrometeor target. Additionally, the system 200 may be utilized to detect properties of the targets 216 in other mediums such as, for instance, any electromagnetic propagation medium that supports multiple modes and exhibits dispersion, such as power transmission lines, optical fiber, free space optics, RF, etc.

In conventional receivers, multipath components that are not reflected from the target are usually regarded as unwanted signal components and detrimental because they mask the clutter returns of interest. In the sensor system 200, however, mitigation of these undesired signal components is not essential due to the fact that these components are generally coherent with the clutter (i.e., they are delayed copies of each other), and hence the polarimetric features of the received signal can still be utilized to sense the desired clutter in the presence of these undesired signal components. Because the system 200 can operate in the presence of a strong line-of-sight (LOS) component and unwanted multipath components, it is a uniquely robust sensor for change detection. The system 200 can also operate in co-channel interference from other wireless systems through excision of beacon pulses that are corrupted by interference. These pulses are discarded instead of being used by the system 200 in the integration processing. Uncorrupted pulses are integrated to obtain high signal-to-noise ratio characterizations of the polarization signatures of the composite signal to increase the system's fidelity.

As noted, the system 200 includes the RF transmitter 210 and a receiver 214 deployed so that the target 216 (e.g., the ground) to be sensed lies in at least one transmission path between the transmitter 210 and the receiver 214 as shown in FIG. 1. The antenna heights, separations, and antenna characteristics are chosen depending upon the scale of the particular application. Qualitatively, the example system 200 operates in the following manner: the transmitter 210 emits RF pulses and/or continuous signals (e.g., signals 212). These pulse signals 212 are reflected by reflectors (e.g. targets) in the environment, including, for example, the ground being sensed. The collection of multipath components arrive at the receiver 214, where in this example dual-polarized antennas capture orthogonally-polarized components of the signal 212 incident at the receive antennas. The processing device 20 processes the captured signals 212 by digitized the data and operating digital signal processing algorithms to estimate the polarization response induced by the transmitted signal 212 in conjunction with the multipath signals as be described.

In particular, the example receiver 214 and processing device 20 together include a low noise amplifier 222, and an RF filter 224 to produce a filtered and amplified signal 212'. The filter and amplified signal 212' is then processed through an analog signal conditioner 226, where the signal is mixed to a low IF and then filtered. The signal is then converted from an analog format to a digital format at the A/D converter 228. A digital signal processor 230 is then utilized to elicit polarization mode dispersion (PMD) features of the received signal. Our course, it will be appreciated by one of ordinary skill in the art that the RF signal could go straight to the A/D converter 228 as desired.

Specifically, in one disclosed example, the digital signal processor 230 receives a channel-impaired version of a known signal, or a signal with a known preamble or training symbols. The vertical and horizontal components are measured for signal quality to determine if the signal is corrupted (e.g., by interference), and if so the received block is excised from further processing. If the signal is not corrupted, the digital signal processor 230 then performs channel estimation on a subcarrier-by-subcarrier basis and computes the Stokes parameters versus the frequency index k. It will be noted that the term "subcarrier" and "subband" are used interchangeably throughout. It will also be understood by one of ordinary skill in the art that other processing parameters may be utilized including, for example, excision, filtering, compensation, statistical characterizations, and/or the application of other signal polarization representations such as Jones vectors.

In another disclosed example, the digital signal processor 230 receives a channel-impaired version of an unknown signal that does not have a known preamble or training sequence. In this instance, the vertical and horizontal components are similarly measured for signal quality to determine if the signal is corrupted (e.g., by interference), and if so the received block is excised from further processing. If the signal is not corrupted, the digital signal processor then forms a covariance estimate and utilizes the result to compute the Stokes parameters versus the frequency index k. In instances where the signal to noise ratio is low, the digital signal processor 230 may use integration where possible to improve the PMD estimate quality.

The estimated PMD signatures are then stored by the processing device 20 and PMD responses from multiple receivers, multiple frequencies, multiple polarization, multiple times, multiple sectors, multiple beams, etc., may be collected to aid in calibration and in the final detection processing. Calibration signals may alternatively be predetermined and provided to the processing device through any suitable means, including, for instance, in a download available through the network 12. The detected PMD signals (herein interchangeable described as "PMD response", "PMD signal", "PMD signature", "PMD curve", etc.) are then interpreted by a detector 232 via comparison of the detected signal with known calibration data and/or previous measurements, to obtain a detected output. Still further calibration can potentially be achieved using topography coupled with ray tracing. The estimated response from the ray tracing for a large number of dielectric constants can be compared with the measured response to identify the particular dielectric constant yielding the closest predicated response.

In at least one example, the detector 232 may compensate for external factors before and/or during interpretation of the PMD signatures. For instance, the polarimetric response of moist soil may change with such external factors as temperature, etc. By measuring these factors (e.g. temperature), the detector 232 may compensate for variations in the external factor. Once interpreted, the results are then output through an output 234, such as the display 60, for reporting and/or any other suitable purpose. Still further, while the present example is disclosed in conjunction with calibration signals, it will be appreciated by one of ordinary skill in the art that the interpretation and/or comparison by the system 200 may be performed by comparing responses from different times, frequencies, beams, sectors, transmitters, receivers, and/or transmit polarizations, etc. to interpret the PMD responses.

In this example where the system 200 is utilized for soil moisture sensing, as the soil moisture varies, the dielectric properties of the soil change, which alters the magnitude and phase of the reflected ground signals, ultimately modifying the polarization behavior of the received signal as a function of frequency. The polarization-frequency (i.e., PMD) response evolves through a continuum of states as the soil moisture changes, leading to polarization-frequency "signatures" that can be interpreted with site specific RF calibration to estimate soil moisture levels.

More particularly, the RF transmitter 210 emits the radio frequency signal 212 as represented by the phasor (Eq. 1):

$$u(t) = A(t)e^{j\omega t} \quad \text{Eq. 1}$$

which is a time varying signal modulated onto a carrier at frequency $\omega = 2\pi f$, where t represents time, $j = \sqrt{-1}$ and A(t) is the complex envelope of the signal having a bandwidth B.

The RF transmitter may transmit a signal that is polarized in a manner such that the polarization state is the same for all of the frequency components of the transmitted signal. Alternatively, the transmitter can transmit a polarized signal that is adaptively set as a function of frequency such as described in U.S. Utility patent application Ser. No. 12/525,299, filed Jul. 30, 2008, titled "Systems and Methods for Adaptive Polarization Transmission", which is incorporated herein by reference in its entirety. The transmit signal adaptation would normally be determined as a function of the PMD features measured at the receiver and would usually be designed to exploit the effects of the propagation channel or environmental factors. The transmitted signal could also be designed or engineered as part of the overall system based on the item or quality to be sensed. As one example, in the case of the detection of contaminants in a homogeneous substance, the transmit polarization could be modified to elicit a null response at a receive antenna for each frequency component of the signal, where nulls would occur only when only the homogeneous substance is present. However, when the contaminant is present, the nulls will lessen due to changes induced by the contaminant, leading to increased energy at the output of the receive antenna.

The transmitted signal propagates through a channel composed of various multipath reflectors with polarization-diverse scattering. The channel, designated by the polarization vector channel $\underline{h}(t,\omega)$, can be represented as a tap-delay filter for each polarization basis component, and the received signal for each polarization component is the sum of delayed and scaled versions of the transmitted signal, where the tap delay filter coefficients will, in general, be different for the two orthogonally-polarized received signal components (Eq. 2):

$$h(t, \omega) = \begin{bmatrix} h^v(t, \omega) \\ h^w(t, \omega) \end{bmatrix} = \begin{bmatrix} \sum_{n=1}^{N} h_n^v \delta(t - \tau_n)e^{-j\omega \tau_n} \\ \sum_{n=1}^{N} h_n^w \delta(t - \tau_n)e^{-j\omega \tau_n} \end{bmatrix} \quad \text{Eq. 2}$$

where N is the number of multipaths, $\pi_n$ is the path delay associated with path n, and $\delta(t)$ represents the Dirac impulse function. Using a frequency-domain representation obtained from use of a discrete Fourier transform, the received signal at frequency subband k is $\underline{X}_k = [X_k^v X_k^w]^T = H_k U_k$, where U, $\underline{H}$, and $\underline{X}$ correspond to the frequency-domain versions of the transmitted signal, the vector channel response, and the received signal vector, respectively. The subscript k corresponds to the frequency subband and the superscripts correspond to the received orthogonally-polarized basis components (e.g., vertical and horizontal polarization).

With the frequency domain representations of the two received orthogonally-polarized components, it is possible to characterize the polarization-frequency behavior through use of Stokes parameters. The Stokes vector for the signal component at subcarrier k, $S_v(k)$ may be obtained from the coherency matrix (Eq. 3, Eq. 4)

$$J(k) = \begin{bmatrix} J_{11}(k) & J_{12}(k) \\ J_{21}(k) & J_{21}(k) \end{bmatrix} = E[\underline{X}_k \underline{X}_k^H] \qquad \text{Eq. 3}$$

Where E[ ] represents the expectation Operator, using $$\underline{S}_v(k) = \begin{bmatrix} J_{11}(k) + J_{22}(k) \\ J_{11}(k) - J_{22}(k) \\ J_{12}(k)J_{21}^*(k) + J_{21}(k)J_{12}^*(k) \\ J_{12}(k)J_{21}^*(k) - J_{21}(k)J_{12}^*(k) \end{bmatrix} \qquad \text{Eq. 4}$$

The response given by the collection of subcarrier channel responses defines the polarization mode dispersion (PMD) response of the channel for the given transmit polarization. We designate this PMD trajectory as the set (Eq. 5)

$$\Gamma_X = \{\underline{S}: \underline{S} \in \underline{S}_v(k), k \in \{1,2,\ldots,K\}\} \qquad \text{Eq. 5}$$

The members in this set are the collection of the received polarization states $\underline{S}_v(k)$ for all subcarriers $k \in \{1, 2, \ldots, K\}$, and the set defines the polarization response induced by the combination of the transmitter and the channel effects. It is this signature that is used for sensing. RF calibration is used to assign soil moisture states to each "signature," to enable translation of the received polarimetric signatures to an estimate of the soil moisture level.

In other possible applications of this technology the received polarized signal components may be weighted with complex weights and coherently summed to achieve a null (or a maximum) at the receiver so that the net received signal power is minimized (maximized) at each frequency subcomponent of the received signal. This is related to other applications of PMD, such as Ser. No. 12/525,297, filed Jul. 30, 2009, titled "Methods for Polarization-Based Interference Mitigation", which is incorporated herein by reference in its entirety, where a fraction of one or more signals incident at the receiver are suppressed so that a cochannel signal of interest can be recovered. However in applications of PMD as a sensor or detector, such as those listed herein but not limited solely to these example embodiments of such a device, only one signal may be transmitted and incident at the receiver. The received signal may exhibit variations due to propagation channel changes caused by the item to be sensed such as a vibration, a change in physical structure or the composition of a target. A received signal may, in one example, be nulled as a function of frequency by the receiver such that under normal or expected conditions no signal energy is registered at the output of the processor. Once configured, changes in the channel response introduced by changes in the target can introduce increased signal energy at the output of the processor, thereby indicating a change.

In other possible applications of this technology the received polarized signal may be nulled at the receiver so that the net received signal is at some expected level which may be some minimum or maximum. In one instance this may be at any predetermined value or may be nulled to a zero value. In other applications of PMD Ser. No. 12/525, 297, filed Jul. 30, 2009, titled "Methods for Polarization-Based Interference Mitigation", which is incorporated herein by reference, a portion of the transmitted and received signals are suppressed or nullified so that the signal of interest can be separated. In applications of PMD as a sensor or detector, such as those listed herein but not limited solely to these example embodiments of such a device, only one signal may be transmitted. The received signal is indicative of the changes caused by the item to be sensed such as a vibration, change in physical structure or composition. A received signal may, in one example, be nulled such that under normal or expected conditions no signal is registered. In these instances the received signal is directly equated to the transmitted signal and any changes can be attributed to expected conditions the transmitted signal encounters.

Figure 3:
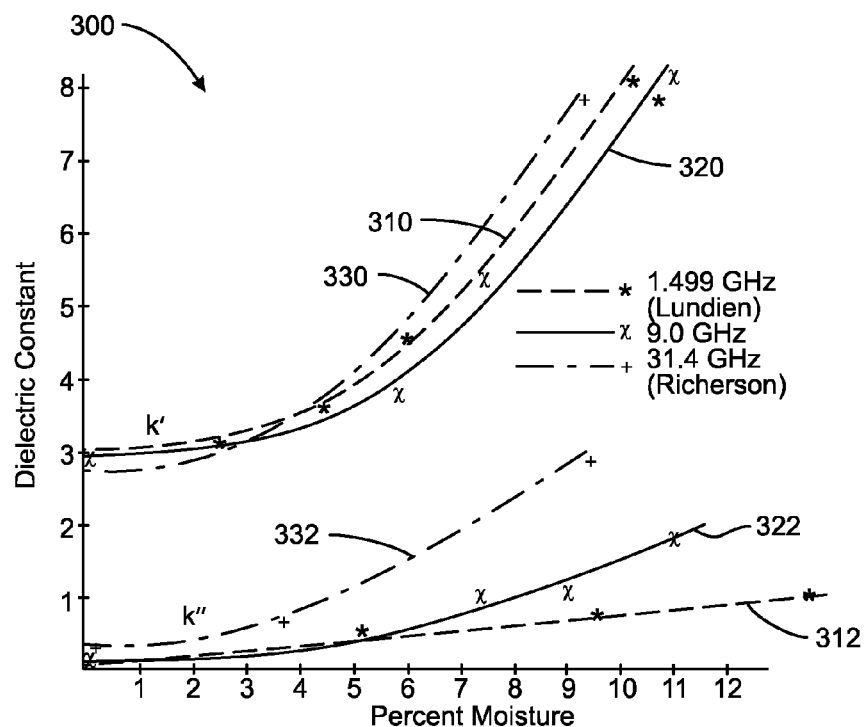
FIG. 3 is an example prior art plot of a dielectric constant versus soil moisture.
Figure 4:
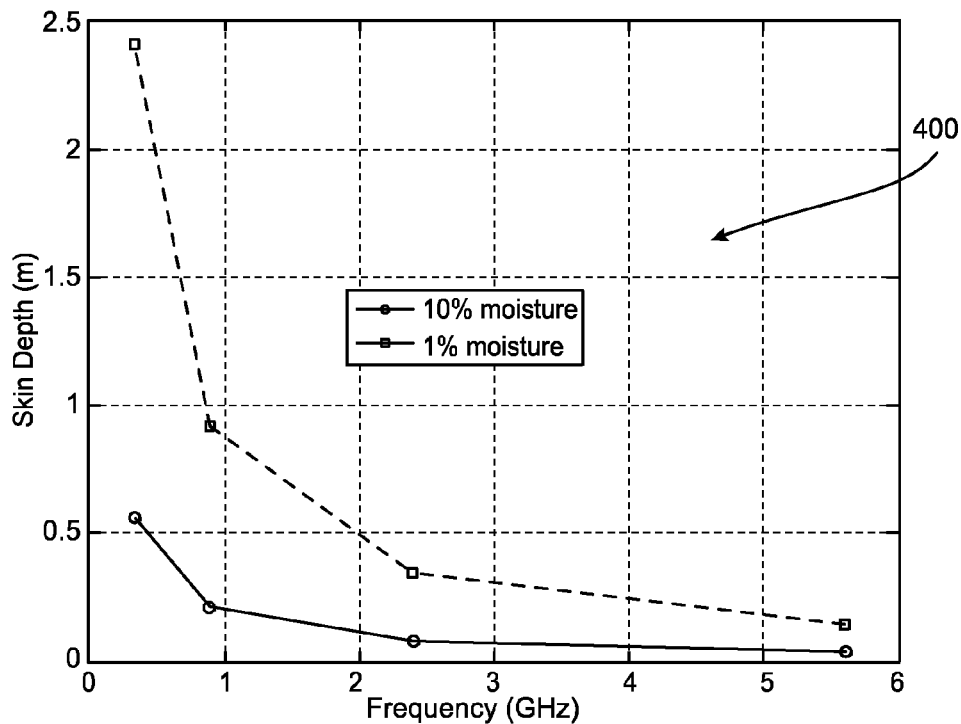
FIG. 4 is an example plot of depth versus frequency based upon the dielectric values of the example plot of FIG. 3.

The polarization-frequency signature represented by $\underline{S}_v(k)$ will be perturbed with changes in the multipath composition due to soil moisture content. To see this, it is noted that the polarization state of a signal reflected from a surface will depend upon several factors including (but not limited to) the complex dielectric constant of the soil state, the polarization state of the incident signal, and the angle of incidence. Example values 300 of complex dielectric constants for a particular soil are shown in FIG. 3 as a function of soil moisture level for three frequencies 1.4 GHz, 9 GHz, and 31 GHz. The upper set of curves (310, 320, and 330, respectively) correspond to the real part of the dielectric constant, and the lower set of curves (312, 322, 332, respectively) to the imaginary part. The measurements indicate increasing dielectric constant values with an increase in soil moisture. The changes in the dielectric properties of a soil with moisture directly impact the skin depth of signal penetration as well as the properties of reflected signal components. The skin depth is given by Eq. 6:

$$\delta = \frac{\lambda \sqrt{\varepsilon'}}{2\pi \varepsilon''} \qquad \text{Eq. 6}$$

and is plotted 400 in FIG. 4 for the dielectric properties from FIG. 3 to illustrate the skin depths versus moisture level for various frequencies (900 MHz, 2.4 GHz, and 5.8 GHz). It will be noted that δ was previously used for the Dirac impulse, while in the present equation, it is the skin depth variable. These skin depths correspond to the "layers" that are characterizes in depth profiles.

Figure 5:
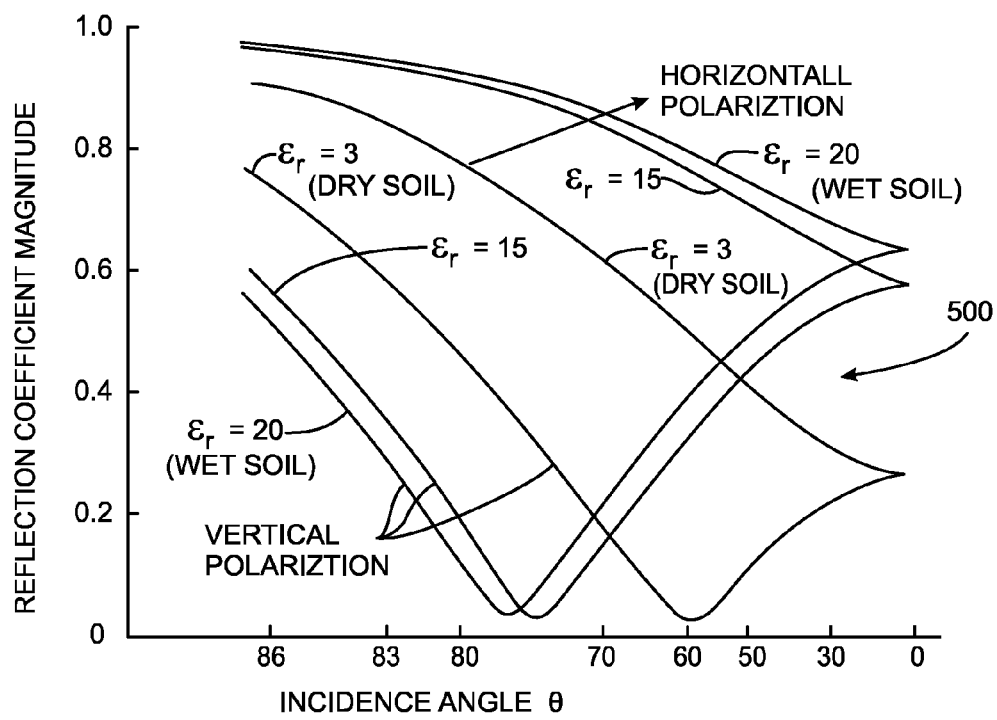
FIG. 5 is an example prior art plot of a reflection coefficient versus incident angle illustrating that different incident polarization components yield different reflection coefficient values versus soil moisture, changing the polarization state of the reflected signal.

Measured reflection coefficients 500 for vertically and horizontally polarized signals at different incidence angles are shown in FIG. 5 for different dielectric constant values. It is observed that the reflection coefficient strongly depends upon the incidence angle and is a maximum at normal incidence. It is also seen that as the soil moisture increases, the reflection coefficient corresponding to the V component (vertical) is reduced, while the magnitude of the H component (horizontal) increases slightly. These changes, as well as associated changes in the phase, result in polarimetric changes in the reflected signal. Thus changes in soil moisture lead to physical changes that can be observed through polarimetric sensing.

As the reflective properties of the soil vary due to changes in moisture content, the received signal composition changes, and the polarization-frequency response also changes, evolving through a continuum of signatures as the moisture in the soil evaporates. In the example system 200, these changes in the polarization-frequency state are detected through minimum distance techniques to identify the calibrated state (measured during the calibration cycle) to which the current state is closest, where each calibrated state is associated with a specific soil moisture level. Assuming a total of M calibration states, $\Gamma_1 \ldots \Gamma_M$, where $\Gamma_m = \{\underline{S}:\underline{S} \in \underline{S}_m(k), k \in \{1, 2, \ldots, K\}\}$ and $S_m(k)$ is a calibrated state, and correspond soil moisture levels $g_1, g_2, g_M$, the measure used to estimate the change between the current states, $\underline{S}_v(k)$, k=1, 2, . . . , K, and the calibrated states is given by Eq. 7:

$$Q_m = \sum_{k=1}^{K} |S_v(k) - S_m(k)|^2, \text{ where } m = 1, 2, \ldots, M \qquad \text{Eq. 7}$$

The estimated soil moisture state is selected to be the one corresponding to the calibrated state that minimizes Q, e.g., the set of $Q_m$ from Eq. 7.

In one implementation of the example system 200, a series of instrumented laboratory-based experiments were conducted to illustrate the application of the RF sensing technology to soil moisture sensing. In this disclose example, the system 200 was used to detect the moisture content of trays of sand (e.g., soil, playsand, etc.) which were acting as the target object 216. The object 216 was wetted, and RF beacon signals from the transmitter 210 (e.g., an IEEE802.11b access point) were transmitted every 100 ms from an external antenna and were received by the receiver 214 (e.g., a second antenna) deployed across from the transmitter antenna with the tray in between. The system was then utilized to measure changes in the polarization signatures of the beacon signals induced by the changing soil moisture levels and to correlate the RF response with the soil moisture estimates derived from capacitance probes used as a control. The beacon signals illuminated the objects and surfaces within the transmission field of view of the antenna, including the three trays of sand. At the receiver 214, a dual polarized antenna was used to collect the signals reflected from the trays and from other objects and surfaces in the vicinity and the signals were digitized using a digital sampling scope and stored on an external hard drive. The collected data were used to synthesize the RF polarimetric signatures.

By way of example, in one configuration, the example system 200 may utilize the following equipment.

TABLE 1

| Equipment | Manufacturer and Model |
| --- | --- |
| Wireless router | Cisco Aironet 1242AG-A |
| Transmit antenna | L3-Com dual polarized antenna HG2414DP-090 |
| Receive antenna | L3-Com dual polarized antenna HG2414DP-090 |
| Low noise amplifier | Mini-Circuits ZQL-2 700MLNW+ |
| RF filter | L3-Com, 2.4 GHz to 2.5 GHz inline filter |
| Digital sampling scope | Agilent Technologies DSQ94O4A |

In addition to the components shown in Table 1, four capacitance probes (EC-5) associated with a CR200 datalogger were also deployed in parallel sections of one of the sand trays. The purpose of these probes was to obtain multiple independent measures of the moisture of soil in the tray. The CR200 datalogger used in the tests was not configured to provide realtime measurement feedback, which is why the Decagon Procheck was used for a realtime indication of sensed soil moisture. In the disclosed example the capacitance probes were calibrated prior to utilization in playsand and an empirical calibration formula to convert the raw voltage output from the probes to the volumetric water content of sand (%) may be developed $\beta = -20.878 + 0.0694 \times \alpha$, where $\beta$ is the converted value of volumetric water content of sand (%), and $\alpha$ is the voltage output from the capacitance probes. The calibration function was subsequently used to estimate the absolute soil moisture level from the measured evaporation cycle data.

The radio frequency receiver 214 collected RF signal snapshots each hour and digitized them for additional post-test signal processing to characterize the polarization-frequency response. The resulting signatures in combination with the CR200 measurements and the Decagon Procheck measurements were then used to assess the performance of the RF approach.

Specifically, in one example test conducted by the system 200, the testing consisted of two evaporation cycles. Prior to the application of water to the trays, the Procheck system was used to measure and confirm the dryness of the soil. To initiate the first cycle, four cups of water per tray were "uniformly" applied to the trays using a watering can, and then the trays were left undisturbed over a period of days while the water in the trays evaporated. Throughout the evaporation cycle, the four probes connected to the CR200 datalogger collected and stored capacitance-based data along with a time and date stamp. The RF receiver 214 collected snapshots every hour and stored these data for eventual post-processing. After approximately four days of collection the reading from the probe connected to the ProCheck meter indicated that that the soil had reached its original dryness state.

Figure 6:
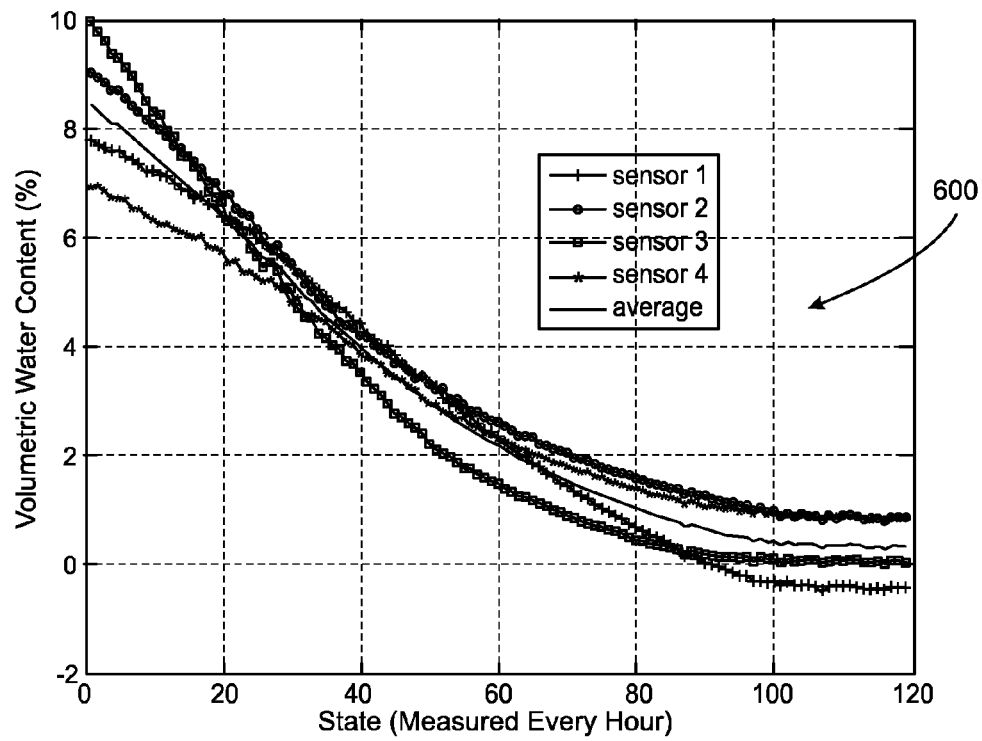
FIG. 6 is an example plot showing calibrated moisture estimates at hourly intervals synchronized to the radio frequency data collected by the example system of FIG. 2.

A plot 600 of the CR200 data collected during the first cycle are shown in FIG. 6, for each probe, where results are shown for the hourly samples that are time-synchronized with the RF measurements. The raw voltage data were converted into moisture estimates using calibration curves for playsand.

The RF data collected by the receiver were also processed to generate PMD signatures. Hourly signatures are illustrated in a plot 700 on a Poincare Sphere in FIG. 7. The signatures may be understood as representing the impact of the multipath reflections (e.g, reflections, scatterings, etc.), including reflections from the soil, measured by the receiver. The signature at the output of the transmitter (prior to propagation) would be represented by a single polarization state on the Poincare sphere for all frequency components of the transmitted signal. The effects of the multipath, including from the soil, result in a dispersion of the polarization state as a function of frequency, where the resulting signature depends upon the composition of the multipath. A review of the plot 700 shows that the signatures are seen to evolve smoothly through a continuum of signature states beginning with the wettest state and ending with the driest state, both which are indicated. Note the ease with which the dry state can be discerned due to the clustering of signatures near the end of the cycle, indicating an important capability of the approach to provide cues when the soil is nearly dried out. The continuous change evidenced by the RF signatures during the evaporation process correlates well with the continuous change observed in the capacitance-based data. Each hourly signature is assigned with the corresponding time-synchronized soil moisture levels derived from the average of the calibrated CR200 measurements.

Figures 7, 8:
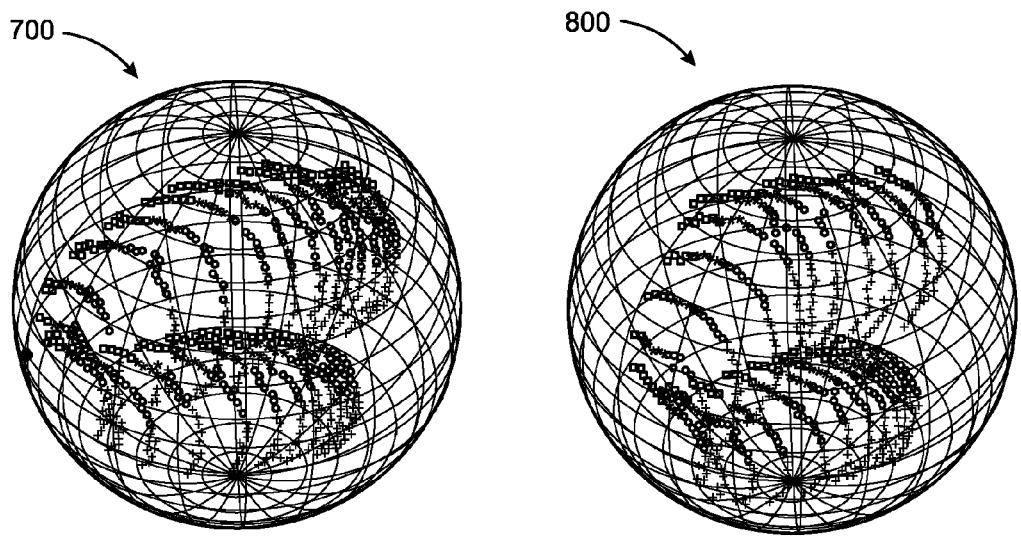
FIG. 7 is an example illustration of various polarization signatures for one example use of the system of FIG. 2.
FIG. 8 is an example illustration of various polarization signatures for another example use of the system of FIG. 2.

As illustrated in the plot 800 shown in FIG. 8, testing associated with a second evaporation cycle was also conducted, although with three cups of water per tray. For the second evaporation cycle, the same procedure was followed to collect both RF and capacitance-based data, and the experimentation was complete after the sand in the trays was dry. As noted, the RF data was processed to generate the PMD curves, sampled at an hourly rate, for the second evaporation cycle. The PMD curves in FIG. 8 map a similar evolution to the first cycle (FIG. 7) because each soil moisture state should yield a repeatable PMD signature. In fact, there is a high correlation between the curves in the plot 800 and the plot 700 in FIG. 7. The difference between the responses in the two cycles is most likely due to the difference in the distribution of the water in the trays that was realized between the cycles, which would lead to perturbations in the PMD curves from cycle to cycle.

Figure 9:
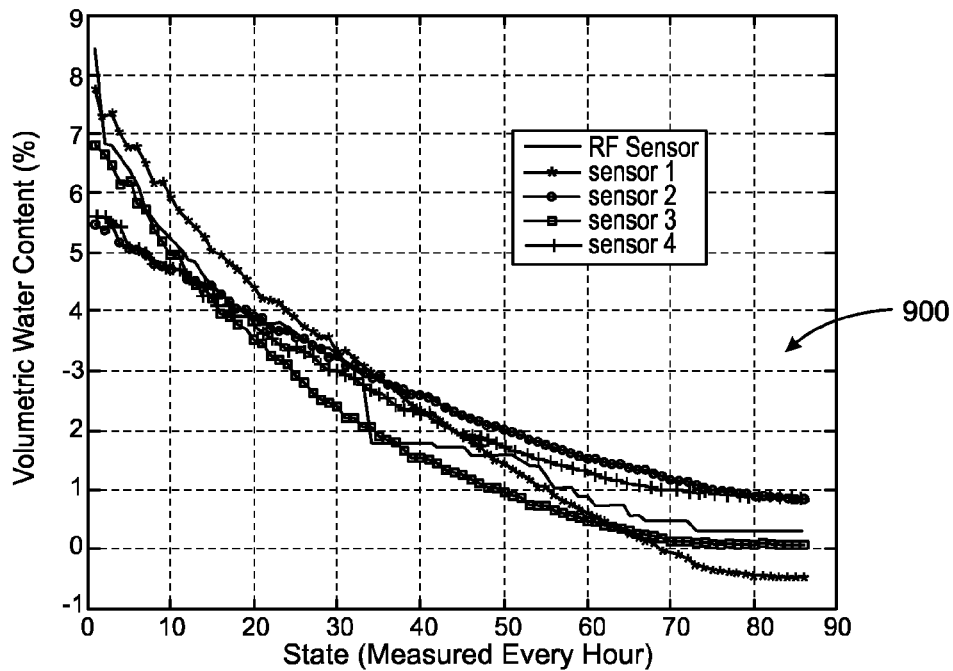
FIG. 9 is an example plot illustrating a comparison of radio frequency sensor soil moisture estimates as obtained from the system of FIG. 2 with capacitance probes embedded in the soil.

In assessing the performance of the polarimetric sensing technique performed by the system 200, it can be seen that the soil moisture can be accurately estimated using the RF calibrated states derived from the calibration evaporation cycle. Specifically, for each RF measurement in the second evaporation cycle, the soil moisture level is estimated by determining the PMD signature from the RF calibration cycle that is "closest" to the RF signature. The corresponding soil moisture level from the RF calibration is then used as the estimate. The soil moisture estimates derived in this fashion for the RF data in the second cycle to obtain "calibrated RF data" are then compared with the calibrated capacitance probe data from the second cycle. The calibrated RF data from the second cycle and the calibrated capacitance data from the second cycle are both plotted by plot 900 in FIG. 9. A comparison of the plotted data 900 shows that the resulting soil moisture estimates fall within the bounds defined by the four capacitance probe and indicates the ability of the RF sensing approach to provide accurate soil moisture measurements in controlled environments using calibration. As the soil nears the final dryout state, the changes in both the capacitance and RF systems exhibit very small changes and when the soil is dried out they exhibit virtually no change. The cue provided by reduced hourly changes in the RF sensor outputs can potentially be used in applications to indicate when the soil is approaching a dried out state.

It will be understood that in addition to a comparison with a calibrated standard, the system 200 may perform a comparison through any suitable comparative means. For instance, the measured PMD signatures may be compared between multiple receivers, may be compared with a calibrated look-up table of signatures, and/or may be compared to a reference state and/or a prior measurement to detect a relative change. Still further, the system 200 may detect changes based upon a time dependent behavior of the detected signatures, may compare signatures between multiple transmitters, and/or may compare the detected measurements with responses at other frequencies, beams, sectors, times, etc. In still other examples, the comparison may allow for detection based upon time dependent behavior of signatures, and/or may be utilized with prediction models to detect and/or predict future outcomes.

Figure 10:
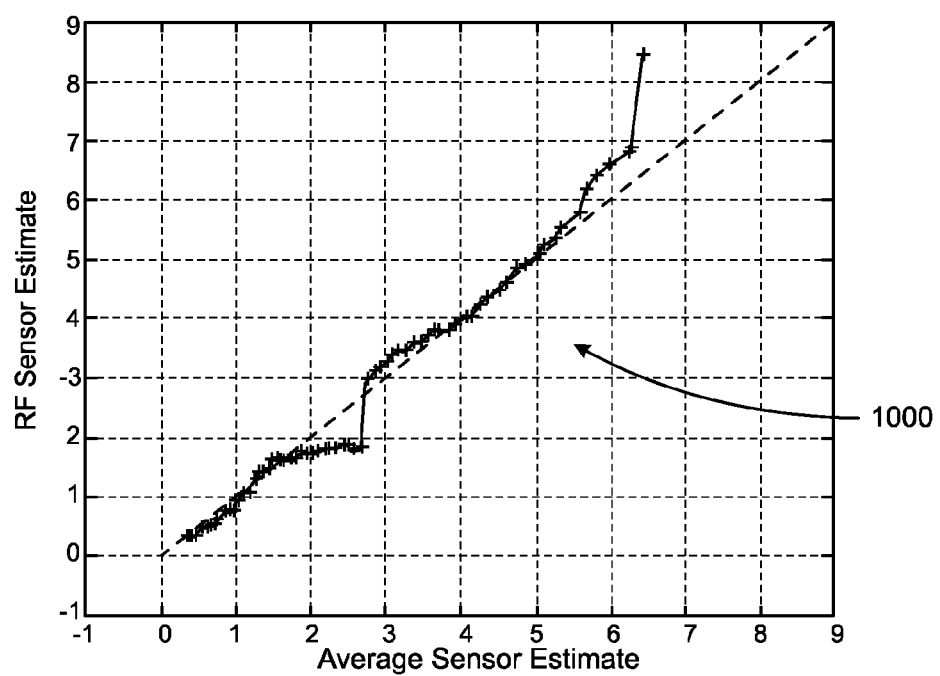
FIG. 10 is an example plot illustrating a comparison of the average capacitance probe response to the radio frequency sensor soil moisture estimates as obtained from the system of FIG. 2.

In this example, the correlation of the RF sensor to the average capacitance probe measurement is evidenced by a plot 1000 in FIG. 10, where perfect correlation (e.g., when the RF sensor output equals the average capacitance probe output) corresponds to responses on the dashed line. There is clearly a strong correlation between the RF sensor output and the average probe measurement.

Hence the RF approach disclosed herein is seen to provide a continuum of changing signatures, consistent with the changing soil conditions in the tray. A practical feature of the performance of the system 200 is that as the soil approaches a dried out state, the hourly change between signatures is small and then become negligible when the soil dries out, suggesting its use as a "drought trigger". Through a calibration procedure, where the measured signatures are assigned to specific soil moisture levels, it can be appreciated that soil moisture estimates can be achieved using the RF measurements that fall within the bounds defined by capacitance measurements. In other words, the measurements are entirely consistent with the capacitance probes, thus showing the effectiveness of the approach.

As noted above, the present example system 200 is disclosed as well suited for soil moisture sensing. In particular, maximizing water use efficiency in agricultural production is increasingly important in an era with increasing global water scarcity and climate change. Soil moisture measurements are a valuable tool for improving irrigation practices. However, there currently are no scalable, remote sensing methods to continuously measure soil moisture content and the present RF polarimetry system 200 may be considered a valuable and cost-effective tool to quantify changes in soil moisture content in real time. In some examples, the system 200 may be integrated into automated irrigation systems that can provide crops with the amount of water needed, when needed, thus benefiting both agriculture and society at large.

For example, the system 200 may be integrally used to develop more efficient irrigation practices, increasing the water use efficiency of crop production. More efficient water use also helps protect our water supplies, one of the most valuable natural resources, and will reduce leaching and runoff from agricultural fields. Because this leachate and runoff can contain fertilizer and pesticides, reducing leaching and runoff decrease the impact of agriculture on the surrounding environment.

While the system 200 is generally illustrated and described as being utilized for soil moisture sensing, it will be understood by one of ordinary skill in the art that the present system 200 may be utilized for various other applications.

As is previously described, the example system 200 may analyze and compare the polarimetric state of RF signals after their reflection from a given target such as the ground and/or soil. In other examples, the present system 200 may be adapted for use with other targets as well. For instance, the system 200 may similarly be utilized in a manufacturing process, such as the processing of food or food products, including processes dependent upon moisture content. More particularly, the present system 200 may by utilized in the drying of foodstuff such as coffee, barley, peanuts, rice, oats, grapes, etc. Use of the system 200 in this manner would replace the foodstuff as the target, and as such, RF signals reflected off these targets may be analyzed for their polarimetric state information to include in one instance PMD.

In another example, as noted above, the system 200 may be utilized to identify moisture and/or or detect other weather and/or other hydrometeor phenomenon such as rain, fog, sleet, snow, hail, clouds, and/or extreme weather. As such, in this example, the target 216 is the atmosphere.

Additionally, the system 200 may be utilized to identify and/or predict moisture and/or ice, such as for instance on a vehicle surface (e.g., ground vehicle, aircraft, wind turbine, airfoil and/or other wing surface), or ground conditions such as icy roads, etc. <<Ice/Water phase change>>

Still further, the present system 200 may be utilized as ground penetrating radar by varying the signal 212 generated by the transmitter 210. For instance, a 400 Mhz signal may typically penetrate the ground approximately 10-15 feet, thus providing ground sensing capabilities beyond the surface soil moisture sensing provided. In this, and all disclosed examples, the system 210 may not rely solely upon a signal of opportunity (e.g., as in a passive system) but rather may generate the transmitted signal (e.g., as in an active system). Additionally, by varying the frequencies of the signal 212, various differing depth of the object 216 may be examined and correlated into a map providing a layered analysis of the target object 216. Additionally, the system 200 may be calibrated to locate different features within the target 216, such as improvised explosive devices (IEDs), structures, pipes, and/or any other item with a different reflection than the target object 216.

Figure 31:
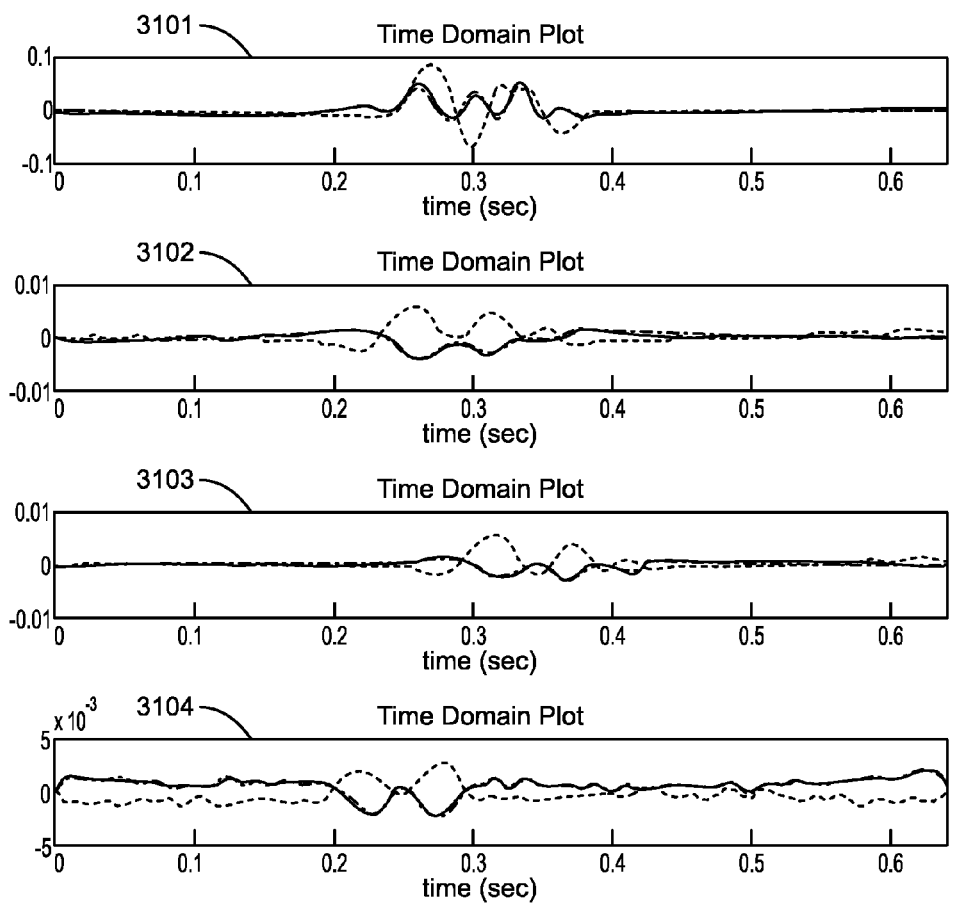
FIG. 31 illustrates an example plot illustrating the detection and/or identification of a food contaminant by monitoring the changes in the polarization mode dispersion behavior.

Still further, the present system 200 may be utilized to detect and/or identify food contamination by monitoring changes in the polarization mode dispersion behavior. The time domain plot of FIG. 31 is one example of such monitoring which could occur. Each plot was developed with a different contaminant placed in a simulated piece of food. A screw 3101, a soft piece of plastic 3102, a hard piece of plastic 3103, and a toothpick 3104 are each independently able of being detected as demonstrated by the plots of FIG. 31 respectively.

As noted above, the present system 200 may be utilized as ground penetrating radar. It will be appreciated by one of ordinary skill in the art that the system 200 may additionally be utilized as any number of types of radars, including, for example, synthetic-aperture radar (SAR). Furthermore, the present system 200 may be utilized to for signal detection and characterization, dehopping of frequency hopping systems, pulse/source associations including for PRI-agile, frequency-agile, PRF-agile, and waveform-agile systems (e.g. to support pulse deinterleaving), target feature detection, and/or target associations for distributed radar.

Still further, the system 200 may be utilized to monitor vibratory systems/events by detecting changes in the PMD response. In one example, the system 200 may be utilized to detect/predict failure analysis in bearings, machinery, etc. Additionally, structures such as buildings, bridges, etc, may be analyzed for vibratory events including failure detection, prediction, and/or analysis. Because the system 200 can detect vibrations, the system may also be utilized to identify voices, sounds, etc., though windows, walls, etc. The system 200 can be used in any application currently serviced by technologies utilizing laser doppler vibrometry. A system using the PMD characterization of a received signal can provide additional information as well. According to the teachings herein, the system 200 can be used as a non-contact vibration transducer system using radio frequency polarimetry, which allows for vibration measurements to be collected remotely and non-intrusively at a distance. Movement or vibration of an object within the radio frequency propagation channel can alter the combined direct, reflected, and multipath radio frequency signals, thereby changing the received signal's polarization. The proposed system 200 can leverage the entire bandwidth of the radio frequency signal by utilizing the frequency-dependent polarization mode dispersion phenomenon that occurs in multipath channels. Such a system would provide at least the same vibration information as a laser doppler vibrometer but would also easier and less expensive to implement and without significant trade-offs in performance. In exemplary demonstration of the capabilities of such a system 200 there are description herein of a pure-tone vibration of tuning forks, the forced and free vibrations of a ringing telephone, and the rotational motion of a desktop fan have been measured and are presented as evidence of this radio frequency polarimetry transducer's diverse capabilities in vibrometry. These examples are meant to be instructive so that others may follow in the teachings presented but do not limit the applicability of this technology. Current state-of-the-art vibration transducer converts vibratory motion into an optical, a mechanical, or most commonly, an electrical signal that is proportional to a parameter of the experienced motion. These current sensors exist in one of several fundamental classifications of vibration transducers exist. One class of current sensors in use are contact or proximity sensor. Contact transducers are mounted directly on the object, usually held in place by screws, cement, wax, magnets, brackets, or simply hands. These contact transducers include: linear variable distance transducers (LVDT), moving coil velocity transducers, seismic transducers, and accelerometers. Proximity transducers are not mounted directly on the object, but they must be mounted very close to the object (typically. less than a few millimeters). They include eddy current sensors and fiber-optic reflective sensors. The PMD based vibrometry sensor described in this application, in contrast to the contact and proximity transducers mentioned above, can operate at longer standoff distance (from several centimeters to several meters) which is hereinafter referred to as remote sensing.

Existing remote sensing vibration transducers include those which utilize ultrasound, magnetic fields, light strobes, and digital cameras. Yet, all of these approaches tend to be limited in their applications within the general field of vibrometry. Those limitations may derive from their specific equipment setup and maintenance requirements, from their limited operating ranges, or merely from their rarity in usage. The most common remote sensing, non-contact vibration transducer is the laser doppler vibrometer or laser doppler velocimetry (LDV), which measures absolute velocity or relative displacement. LDV reflects a laser light beam off of the object under test, and measures the backscattered light for a Doppler frequency or phase change with respect to a reference light beam usually via a Michelson interferometer. The use of a laser beam allows for a very small target point of measurement on the vibrating object without the addition of any mass or load. But, the laser itself greatly increases the expense, size, and complexity by virtue of its installation and calibration of this sensor as compared to an accelerometer, for example. Vibration transducers are critical components in the measurement and analysis of vibrations. Accurately converting the mechanical motion into an electrical parameter, spanning a wide frequency range and a large dynamic range, is paramount. Yet some vibrometry applications do not lend themselves well to the intrusive mounting of contact sensors or even proximity sensors. Therefore, non-contact transducers capable of remote sensing should be very useful. Therefore, a less expensive and easier-to-use remote-sensing vibration transducer should be of great interest. The remote sensing approach based on RF scattering described herein provides a cost-effective alternative to expensive laser-based systems by using RF electromagnetic signals and monitoring the polarization, which captures both relative phase and amplitude differences in RF signals.

In one embodiment of the invention, a remote RF vibrometer can use the polarimetric mode dispersion (PMD)

characteristics of a sensed electromagnetic wave to measure the vibratory response of an object. In such an instance, the electromagnetic wave's polarization properties are analyzed where every electromagnetic wave is composed of an electric field and a magnetic field. The polarization of that wave can be defined as the direction in which the electric field is aligned in the plane transverse to the propagation direction throughout the passage of one full cycle. Typically, both the electric field's magnitude and angle will vary during wave propagation, thereby tracing an ellipse in the plane perpendicular to its direction of travel. Hence, the most general polarization classification is called elliptical polarization, which may rotate in either the left-handed or right-handed direction. A special case, where the minor axis of the ellipse is zero, is called linear polarization, which may be tilted at any angle, but Horizontal polarization (H, 0°) and Vertical polarization (V 90°) are typically used as a reference basis. Another special case, where the major and minor axes of the ellipse are equal, is called circular polarization, which may be either left-handed circular (LHC) or right-handed circular (RHC). Well established techniques exist to measure and graphically depict every possible polarization state on a Poincaré sphere. The modulation of an RF signal by a vibrating or rotating object is discussed in *The Micro-Doppler Effect in Radar* by Victor Chen; however, the vibrational analysis presented therein is based on micro-doppler shifts, whereas the disclosed invention of this application proposes using polarization, and specifically PMD, as the metric for analysis. As previously noted, the polarization of RF signals has been used previously in various remote sensing applications; however these references do not teach using the sensed PMD characteristics as a vibration transducer.

In a preferred embodiment, RF polarimetry is employed to detect the relative change of polarization-frequency behavior as determined by the coherent data collection and analysis from a dual-channel, dual-polarized (H and V) receive antenna. This coherent polarization technique leverages the phenomenon of PMD to uniquely characterize the polarization 'signature' of an RF signal. A moving or vibrating object within the RF signal's propagation path can create multipath variations that in turn can create time-varying changes to that polarization-frequency signature. Temporally analyzing these changing polarization signatures allows mechanical motion to be sensed as an electrical signal in a RF polarimetry remote-sensing vibration transducer. In a manner similar to the method described for measurement the vibratory motion of an object (i.e. displacement over time), it is possible to measure the velocity of an object. In other cases an objects attitudinal rate of change or angular velocity components may be detectable through its PMD response.

Figure 11:
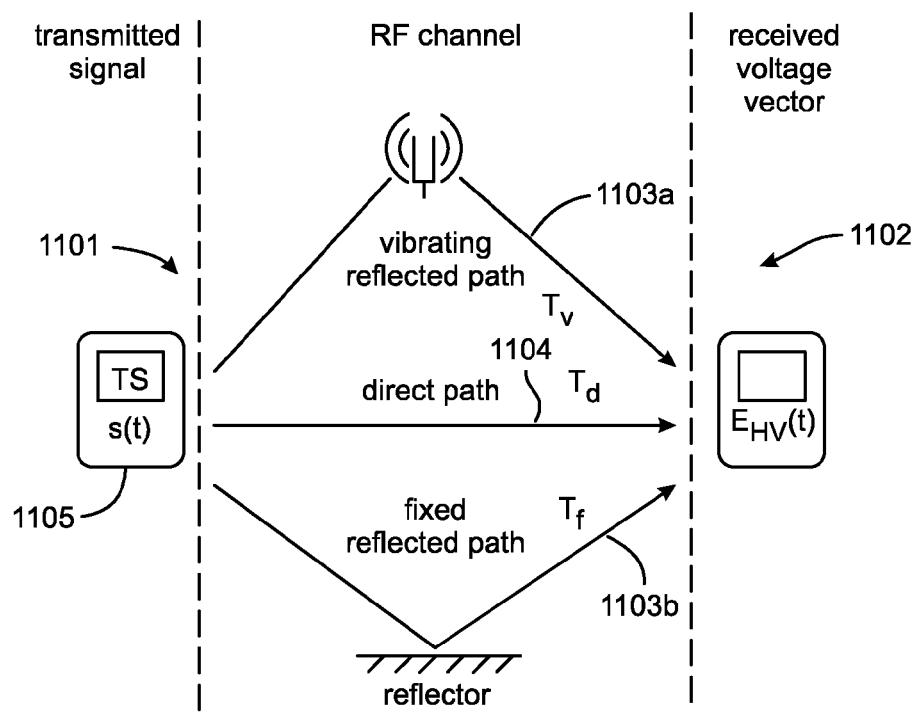
FIG. 11 illustrates an example measurement of a vibrating system, such as a radio frequency measurement of a tuning fork.

The vibration transducer system disclosed herein, an example of which is depicted in FIG. 11 employs an RF transmitter subsystem (TS) 1101 and a receiver subsystem (RS) 1102. An RF signal, s(t), where in one instance this may be 802.11b WiFi, which is transmitted from the TS 1101 to illuminate the vibrating target with RF energy. The system's geometry is arranged so that some of the reflected energy 1103 scattered by the target can be sensed at the RS 1102. As depicted in FIG. 11, the received electric field voltage vector EHV (t), which has as its elements H and V orthogonally-polarized received signal components, can include multipath signals scattered by the target, but may also include a direct path signal 1104 (the path from the transmit antenna to the receive antenna without any reflections, also called the line-of-sight path) and one or more multipath components reflected from other reflecting surfaces in the environment. The propagation distance for each path will generally be different, leading to different times-of-arrival for the paths (i.e., different path delays). The line-of-sight path maintains the original polarization state, but the reflected signals can change their polarization state upon reflection, a phenomenon that is commonly referred to as "depolarization". The relative delay differences between the received signal components coupled with depolarization leads to PMD behavior which is a signal feature that can be measured at the RS.

A received electric field voltage vector $\underline{E}_{HV}$ (t) can be considered in a multipath RF channel and may be represented by delayed and scaled versions of the transmitted signal 1105, s(t):

$$E_{HV}(t) = \begin{bmatrix} \sum_{i=1}^{N} \alpha_i^h s(t-\tau_i) e^{j2\pi ft} + \sum_{i=N+1}^{N+M} \alpha_i^h(t) s(t-\tau_i) e^{j2\pi[f+f_d(t)]t} \\ \sum_{i=1}^{N} \alpha_i^v s(t-\tau_i) e^{j2\pi ft} + \sum_{i=N+1}^{N+M} \alpha_i^v(t) s(t-\tau_i) e^{j2\pi[f+f_d(t)]t} \end{bmatrix} \quad \text{Eq. 8}$$

where the $\alpha_i^h$ and $\alpha_i^v$ correspond to the relative complex scale factors for a path i (which depend on propagation losses, reflection coefficients, etc.), the $\tau_i$ correspond to the delay associated with path i, f is the carrier frequency, and $f_d$ corresponds to a Doppler frequency shift. The right side of Eqn. (8) includes two terms for each polarization component. The first term corresponds to the response from the line-of-sight component and from other fixed reflectors in the environment (a total of N paths). The second term corresponds to the time-varying response from the vibrating target (a total of M paths), and it is responsible for introducing time-varying changes into the polarization response measured at the receiver. When the non-target reflectors in the environment are stationary or change slowly relative to the measurement interval, polarization changes in the received signal will arise principally from changes in the scattered energy reflected from the target as it vibrates.

Figure 12A:
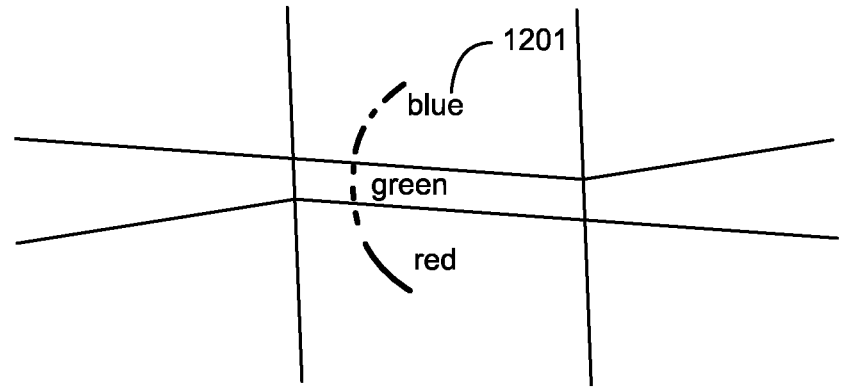
FIGS. 12A and 12B together illustrate an example plot of a PMD response received from the example vibrating system of FIG. 11 as plotted on a Poincaré sphere.

PMD may be understood as a spread in the polarization state observed at the RS 1102 as a function of the frequency subband of the received signal, and it can be visualized on the Poincaré sphere. The polarization response will vary smoothly from the lowest RF subband to the highest, as shown in FIG. 12, creating a smooth curve 1201 on the sphere. By way of example, the simple dispersion pattern shown in FIG. 12 is indicative of a multipath environment with one direct 1104 and two multipath components 1103 (e.g., N=2 and M=1), similar to the simple model represented in FIG. 11. More complex dispersion patterns result when the multipath structure is more complex. In general, PMD characteristics are determined by the transmitted signal polarization, the antenna directivity, the channel multipath structure, and the signal bandwidth. As the multipath structure from the target changes with time (e.g., due to a vibrations), the PMD response also will change with time. For cyclic vibrations the PMD response will be cyclic at the same rate. This phenomenon forms the basis of the transducer system.

The polarization state associated with the received electric field components, $\underline{E}_{HV}$ (t), may be characterized using Stokes parameters, such as those presented by Eq. 4. The Stokes parameters may be derived with the addition of computing the Stokes parameters as a function of the frequency components of the received signal which is in effect characterizing the PMD of the received signal. The quality of the measured PMD behavior is dependent upon the signal to noise power ratio (SNR) of the received RF signal as well as the time interval over which the signal can be integrated. PMD estimates exhibit variations about the true polarization states that depend upon the SNR where higher SNRs yield improved polarization state estimates. Generally, it may hold in certain situations that an effective SNR of 40 dB leads to errors that exhibit a 1 degree error variation on the Poincaré sphere. Stokes parameters characterizing the received signal polarization states are estimated from the received electric field vector. Stokes parameters characterizing the received signal polarization states are estimated form the received electrical field vector by first computing the coherency matrix, J, by use of an expectation operation denoted by $\langle E_{HV} E_{HV}^\dagger \rangle$ in the following equation.

$$[J] = \langle E_{HV} E_{HV}^\dagger \rangle = \begin{bmatrix} \langle E_H E_H^* \rangle & \langle E_H E_V^* \rangle \\ \langle E_V E_H^* \rangle & \langle E_V E_V^* \rangle \end{bmatrix} \quad \text{Eq. 9}$$

The four Stokes parameters, $S = [S_0\ S_1\ S_2\ S_3]$ are then calculated by the following equation.

$$S_0 = \langle E_H E^*_H \rangle + \langle E_V E^*_V \rangle$$
$$S_1 = \langle E_H E^*_H \rangle - \langle E_V E^*_V \rangle$$
$$S_2 = \langle E_H E^*_V \rangle + \langle E_V E^*_H \rangle$$
$$S_3 = j\langle E_H E^*_V \rangle - j\langle E_V E^*_H \rangle \quad \text{Eq. 10}$$

$S_1$ represents the unit vector in the direction of horizontal polarization, $S_2$ the unit vector in the direction of slant 45° linear polarization; and $S_3$ the unit vector in the direction of left-handed circular polarization. Ideally, the signal will be completely polarized and the total power density will be $S_0^2 = S_1^2 + S_2^2 + S_3^2$. In practice, the signal will not always be fully polarized. Therefore, the signal is divided into a large number of contiguous subbands to ensure that signals within each subband exhibit a high degree of polarization. By doing so, the above polarization state representations can be applied on a subband-by-subband basis. The resulting polarization states versus frequency correspond to the PMD response.

Figure 13:
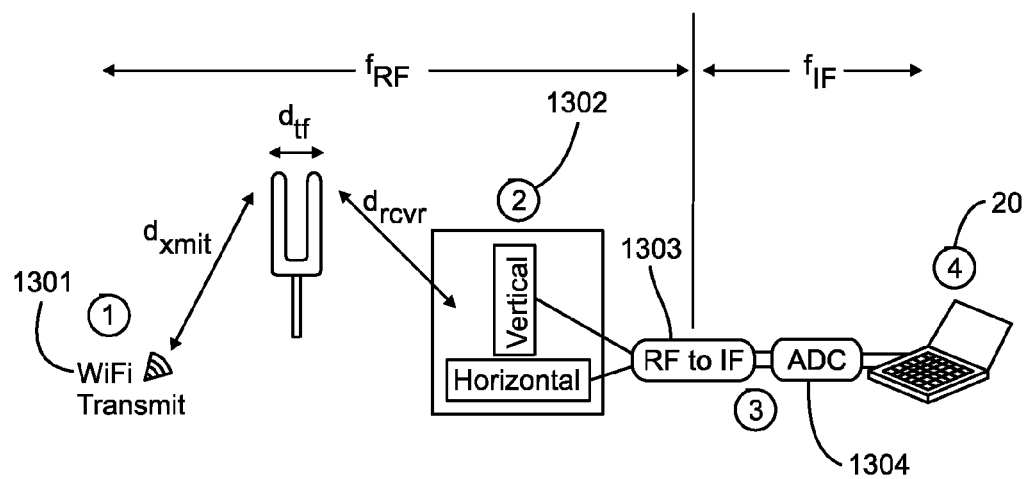
FIG. 13 is an example vibration sensing system in accordance with the teachings of the present disclosure.

The four components of an exemplary RF polarimetry vibration transducer are labeled in FIG. 13 and may include a WiFi transmitter and antenna 1301, which is used to provide the transmitted RF signal and may transmit a 802.11b signal for instance; a dual-polarized (H and V) receive antenna 1302, which is used to capture the orthogonal components of the RF signal's electric field vector, from Eq. 8; a coherent, dual-channel RF-to-IF plus ADC module 1303, which is used to convert the RF signal (such as 2.4 GHz for example) down to some intermediate frequency (IF) signal (such as 60 MHz for example) and then to sample that IF signal using an analog-to-digital converter (ADC); and a processor 20 or computer routine used to implement a signal processing algorithms that processes the sampled IF voltage signals to measure and interpret the PMD curves.

A topology involving spatially separated TS and RS, as shown in FIG. 13, is called a bistatic configuration. A topology where the TS and RS are co-located, called a monostatic configuration, can also be employed. In either case, the main subsystem is the coherent, dual-channel (H and V) receiver 1302 used to receive the RF signals. The received RF field may have a carrier frequency at any value above the IF frequency. In one instance this may be 2.4 GHz; however any frequency may be chosen and does not limit the teachings herein. In other applications that will be discussed higher frequencies may be desirable. An RF-to-IF converter 1303 is used to translate the RF signal to an intermediate frequency, such as 60 MHz, before it is sampled at a rate of 400 MSa/s (mega-samples per second) by the ADC 1304. The H and V components of this samples signal vector are analogous to the H and V components of the electric field from Eq. 8. Variables that contain two channel data are identified by the "HV" subscript (e.g., $x_{HV}$, $y_{HV}$, $Y_{HV}$).

The received electric field voltage vector, $x_{HV}(t)$, which is the IF version of $\underline{E}_{HV}(t)$ from Eq. 8, is digitally captured and down converted to a complex baseband vector. The downconversion is achieved through the following operation:

$$y_{HV}(t) = x_{HV}(t) e^{j2\pi f_{IF} t} \quad \text{Eq. 11}$$

where $f_{IF}$ is the intermediate frequency, such as 60 MHz, and t represents discrete time samples. The complex baseband signal is then transformed to the complex frequency-domain vector, Y. The discrete Fourier transform (DFT) is performed on an N-length block of time-domain samples to transform the discrete voltage data into complex frequency domain signals $$Y_{HV}(k) = \sum_{n=0}^{N-1} y_{HV}(t) e^{-j2\pi kn/N} \quad \text{Eq. 12}$$

where k corresponds to the center frequency of the resulting N frequency subbands. In one embodiment, N may equal 1000. When, in one instance, the transmitted RF signal spans a frequency bandwidth of 22 MHz (measured null-to-null in 802.11b format), approximately 400 of the sub-carrier frequencies within that 22 MHz bandwidth contain signal energy; therefore, Stokes parameters are computed for these frequency subbands. Hence, for each N-length block of time samples, YHV yields 400 sets of Stokes parameters, (Sx; Sy; Sz) that can be plotted on the Poincaré sphere to obtain a PMD response curve. The coherency matrix of Eq. (9) can be calculated for each subband using:

$$[J(f)] = [Y_H^*(f)\ Y_V^*(f)] \begin{bmatrix} Y_H(f) \\ Y_V(f) \end{bmatrix} \quad \text{Eq. 13}$$

and Equations (10) can be used to solve for the corresponding four Stokes parameters for each frequency subband. The parameters are normalized to exactly place their polarization state on a unit sphere, such that $S_x^2(f) + S_y^2(f) + S_z^2(f) += 1$. These Stokes parameters can then be plotted on the three dimensional Poincaré sphere to graph the PMD curve, as shown in FIG. 12. This PMD curve is comprised of 400 individual polarization points, colored according to the rainbow in their frequency order, from the lower frequency subcarriers in red to the higher frequency subcarriers in blue.

A dynamic PMD curve may be created by applying the static PMD curve technique discussed in the previous section repeatedly over time. This dynamic PMD curve analysis converts the mechanical motion of a vibrating object into the temporal polarization-based parameter creating the vibration transducer. One general method is as follows: extract a suitable time window from the received data, calculate the static PMD curve of that windowed subset, take a suitable time step forward in the received data, and repeat. The resulting array of temporal PMD curves will contain time-varying behavior corresponding to the dynamics of the vibration(s). Further techniques to distill the array of PMD curves down to a single time-varying parameter are detailed herein.

Dynamically stepping a time window across the received polarized data, $x_{HV}$, requires selecting the window size and the step size. The primary trade-off when selecting a window size is between increasing the resolution of the calculated time-domain vibrational data (i.e., selecting the smallest window size possible) versus increasing the accuracy of the PMD curve (i.e., select the largest window size possible). The smallest window size possible is essentially limited by the frequency, bandwidth, and sample rate of the IF received signal. The static PMD curve calculation, detailed in the previous section, relies upon the DFT transformation of the captured receive voltage data. Therefore, the extracted window subset of $x_{HV}$, used in this dynamic analysis, must be large enough (i.e., contain enough data samples) to represent the complex frequency information for all sub-carrier frequencies within its bandwidth. A particular DFT analysis (including filtering, decimation, and DFT) utilized here performs best with no fewer than 10,000 samples (at the sample rate of 400 MSa/s (mega samples per second)), so a lower limit on the window size may be set at 20 us. The number of samples in a window is simply the time (in seconds) multiplied by the sample rate. While discussion herein leads to window step size being defined by a specific number of seconds, it should be obvious that number of samples could also be used. The largest window size possible is not limited by the PMD calculation, but rather by the desired vibrational analysis. Larger window sizes will produce 'cleaner' PMD curves by averaging out noises, but they will also average away higher frequency (shorter period) signals from the time-varying vibrational data.

TABLE 2

Frequency SNRs (in dB) over window sizes

| Frequency (Hz) | Window Size | | | | |
|---|---|---|---|---|---|
| | 100 µs | 500 µs | 1 ms | 5 ms | 10 ms |
| 10 | 66 | 73 | 76 | 82 | 84 |
| 100 | 56 | 63 | 66 | 70 | 16 |
| 1000 | 46 | 50 | 16 | 19 | 11 |

Table 2 data, which was taken from calculations and may differ from specific empirically measured values depending on the environment, clearly shows the effect of selecting a larger window size. The small window size of 100 µs can accurately capture the presence of 10, 100, and 1000 Hz signals with SNR levels>45 dB, but the averaging effect of the wider 1 ms window can obscure the 1000 Hz signal (SNR<20 dB), and the wider yet 10 ms window obscures all but the 10 Hz vibration. An appropriate window size should be selected depending upon the vibrational frequencies of interest. For some vibrational sensing applications such as those which occur with a frequency of less than 10 kHz, a window size of 1/10 kHz=100 µs may be selected. Other window sizes may be selected. Those other window sizes may be based on the target frequency of interest. Once the window size is chosen, the selection of step size may be based on the desired sampling rate. A smaller step size results in more vibrational data samples per second increasing the transducer's effective sampling rate. And, from basic frequency analysis theory which is known by those skilled in the art, higher sampling rates allow for wider detection ranges (higher Nyquist rate) and more precise frequency identifications (less spectral leakage and less picket-fence effect). Therefore, the smaller the step size the better. However, this advantage is ultimately limited by the chosen window size. As mentioned previously, the averaging effect of the window size imposes an upper limit on the discernible frequencies. So, the theoretical minimum step size of one sample would needlessly burden computations and memory requirements, if for example a given a chosen window size of 100 µs was also selected. In a preferred embodiment of the polarimetry vibration transduce a step size of 0.1 to 1 times the chosen window size. Note that this step size corresponds to the sampling rate of the vibrational data. Per the Nyquist sampling rule, frequencies greater than one-half of this sampling rate will be aliased. A step size of 20 µs corresponds to a sampling rate of 50 kHz; therefore, all frequencies below 25 kHz should be uniquely detectable.

Figure 12B:
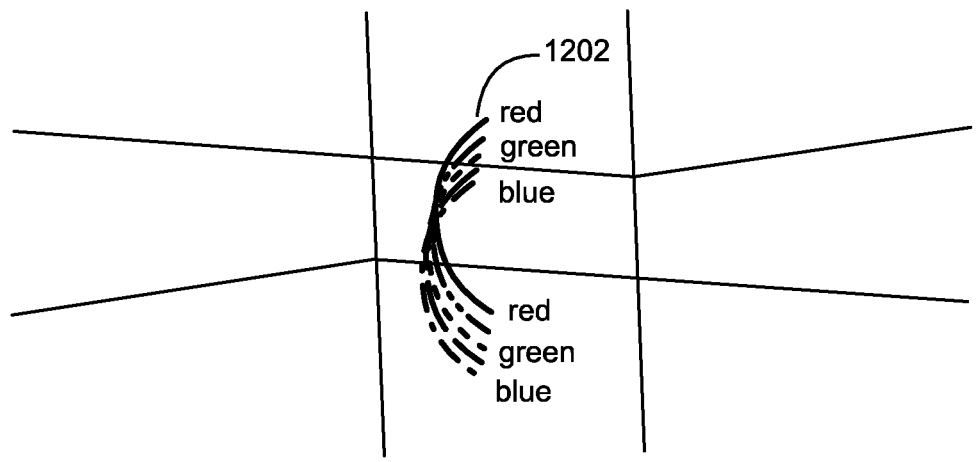

Data in each windowed section is extracted. Sensed RF energy is converted to a voltage signal and the PMD curve is calculated for that data as discussed in the proceeding sections, the window is stepped forward in time, and the procedure is repeated and then time-varying PMD curves can be created. (This plot uses the same PMD curve shown for the static case in FIG. 12A.) In the following example a 100 Hz vibration is described; however, it should be obvious to one skilled in the art that any other frequency could be used and such a choice would then rationally follow the same description. In FIG. 12B, The temporal PMD curves 1202 can be seen to 'move' on the Poincaré sphere with a period of 10 ms (1/100 Hz). Only half (5 ms) of the full periodic motion is shown since the second half would simply overlay the first half due to the expected symmetrical sine wave. The time-varying PMD curves are displayed every 0.25 ms (20 PMD curves over this 5 ms half-period), and the color of each PMD curve is color coordinated (e.g. rainbowed) from blue to green to red according to its location in time (rather than according to its frequency as in FIG. 12A). The Cartesian coordinates corresponding to the Stokes parameters (Sx; Sy; Sz) are convenient for plotting PMD curves on the Poincaré sphere. But, the normalization that places the polarization points on the unit sphere, effectively reduces the three coordinates to two dimensional (unit) polar coordinates, (SΘ; SΦ), without any loss of information. This transformation reduces the three Stokes coordinates to two, but each of those variables is still a time-varying vector of 400 sub-carriers, due to the PMD effect. So, these multiple sub-carriers must be combined to arrive at the goal of a single time-varying signal.

A time-varying array of PMD curves can be constructed using the temporally stepped window plus the static PMD curve calculation technique described above and shown in FIG. 12B. It also may be desired to have a vibration transducer with the output of a single time domain parameter may. Any one of a given channels sub-carriers could be chosen as the one vibrational parameter to interrogate, but that selection would merely discard the additional information from the other sub-carriers. While choosing an arbitrary subband or even a specific subband designed or otherwise known to provide representative vibrational information is within the scope of the invention disclosed herein, a preferred embodiment of the invention uses a time-domain average to constructively combine, in one instance the 400 subcarrier polarizations. Simply averaging each of the time-domain Stokes parameter coordinates, (Sx; Sy; Sz) for Cartesian or (SΘ; SΦ) for polar, over the 400 sub-carriers would produce the center of mass, or centroid, of the PMD curve. Consequently, the 400 data point curve could be represented by a single (average) data point at each location in sampled time. This centroid technique is particularly useful for time domain analysis or time domain plotting. The advantage of the centroid method is that this single time domain signal can be converted via a single DFT to the frequency domain. This advantage has generally been found to outweigh the drawback of any cancellation of individual frequency components or the loss of specific PMD effect or PMD signature.

Figure 14A:
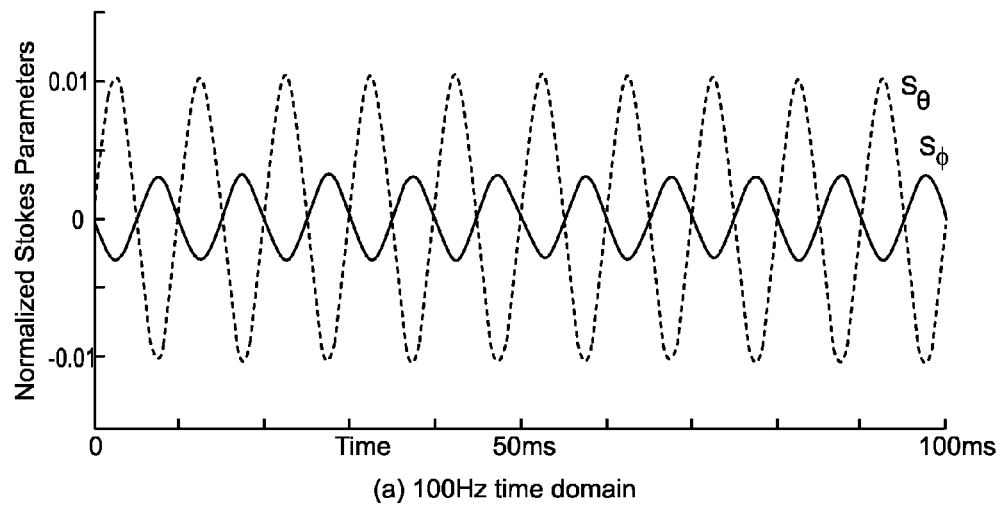
FIG. 14 is an example plot of the time and frequency domain of the Stokes parameters centroid.
Figure 14B:
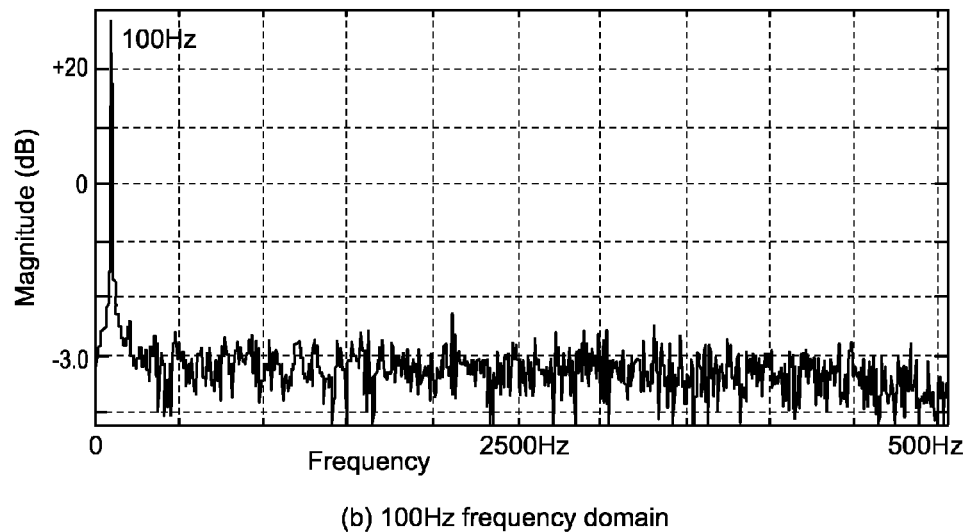

The dynamic RF polarization analysis described in this section provides the techniques for converting simulated RF polarization data into a time-varying parameter suitable for use as a vibration transducer. Now, for completeness, basic harmonic analysis may be performed on this temporal vibrational data. Continuing with a past example, a 100 Hz vibration is once again used to demonstrate the invention. First, the time domain plot of the Stokes parameters centroid is given in FIG. 14 over 100 ms. Ten complete periods of the 10 ms period signal are clearly evident in both the $S\theta$ and $S\Phi$ polar coordinates. (This plot uses the centroid from a window size of 100 μs and a step size of 20 μs.) Next, the signal is converted to the frequency domain via DFT. Once again, the signal at 100 Hz is clearly evident demonstrating the RF polarimetry vibration transducer potential to detect this simple vibration example.

There exists at least two primary effects from the RF signal's propagation through its channel. First, the RF signal will experience reflecting, scattering, multipaths, etc. that will combine to create PMD effects, and second the vibrating object will impart its variations into the RF signal's received polarization at the frequency of the vibration. In one embodiment of the invention such as that shown in FIG. 13 a bistatic setup for the transmitted signal may be used. The transmitted signal may contain signals at two frequencies where $f_{RF}$ is the center frequency of the transmitted RF signal, which propagates through the channel and is the 'carrier' for both the PMD effect and the vibration sensing effect and where $f_{IF}$ is the center frequency of the hardware downconverted signal, which contains the PMD effect and vibrational effect information of the $f_{RF}$ signal at a lower frequency. In this instance, both the $f_{RF}$ and $f_{IF}$ signals have the same bandwidth ("BW"). Such a system synthesizes the data vector $x_{HV}$ at the frequency $f_{IF}$, which is the signal frequency at the input to the ADC 1304. But, it includes the propagation channel effects associated with the carrier frequency $f_{RF}$. Since the receiver block ultimately processes this data as two separate, but coherent signals, two separate signals are created here: H polarization and V polarization.

As has been used in previous examples, a 802.11b Wi-Fi transmitter set to Channel 6 may be used and in this instance the $f_{RF}$=2:437 GHz and BW=22 MHz. The downconverter is designed such that $f_{IF}$=60 MHz. Other channels or wireless communication standards may be used and fall within the scope of the invention described herein. In such instances the center frequency and bandwidth specific to those systems would be known quantities easily discernible to those operating with these systems. PMD impairments may be included by modulating the Horizontal channel amplitude in a continuous manner with frequency while keeping the Vertical channel amplitude constant. And, the vibrational effect may be included by modulating the Vertical channel phase while keeping the Horizontal channel phase constant. Including the PMD effect requires modeling over the entire signal bandwidth where the signal's polarization must vary smoothly over that bandwidth. One method of varying a wave's polarization is to adjust the relative amplitude of its two orthogonal bases (H and V), and one method of creating signal bandwidth is to sum together sinusoids in the time domain that span the desired frequencies. These two techniques are used together to create the PMD effect in this model by creating 20 μs sub-segments represented by $x_{HV}^{PMD}$ and calculated according to the following equation.

$$x_{HV}^{PMD} = \begin{bmatrix} x_H^{PMD}(t_m) \\ x_V^{PMD}(t_m) \end{bmatrix} \qquad \text{Eq. 14}$$

$$= \begin{bmatrix} \sum_{l=1}^{L} A_{Hl}\cos(2\pi f_l t_m + P_H + \eta_l) \\ \sum_{l=1}^{L} A_V \cos(2\pi f_l t_m + P_{Vl} + \eta_l) \end{bmatrix}$$

Where $f_l=f_{IF}+f_l^{PMD}$ and $f_l^{PMD}$=−BW/2 to BW/2 set ¹⁄₂₀ MHz. Further L=BW/(¹⁄₂₀M)+1, and $t_m=t_{0m}+(m-1)$ with $t_{0m}=1/f_s$, and where $\eta_l =2\pi\text{rand}(1)$ to randomize the cosines' initial phases to prevent the time domain summation from resembling a delta impulse function The PMD effect is included by using a function off as on channel's amplitude, such as:

$$A_{Hl} = \frac{\left|\frac{2f_l^{PMD}}{BW}\right|^3 - BW}{BW} \qquad \text{Eq. 15}$$

$$A_V = 1$$

The resulting curve of this PMD impairment is shown in FIG. 12. The polynomial of Eq. (15) was chosen to produce a curve similar in shape. The effect of the vibrating object needs to be included by adjusting the relative phase of its two orthogonal basis components H and V. In one embodiment the phase of the H channel is set to 0 ($P_H$=0) and the phase of V channel may be modulated according to the following equation:

$$P_{Vl} = 2\pi \left[\frac{d(t_m)}{\lambda_1}\right] \qquad \text{Eq. 16}$$

The value $d(t_m)$ is the propagation distance and calculated by $d(t_m)=d_{xmit}+A_t \sin(2\pi f_t t_m)+d_{revr}$ and $A_t$ and $f_t$ are the amplitude and frequency of the vibrating target, respectively. The value of $\lambda_1$ is the transmit signal's wavelength given by $\lambda_1=c/[f_{RF}+f_l^{PMD}]$ and c is the speed of light. Taken together these equations and Eq. 14 through 16 lead to being able to calculate the following:

$$x_{HV} = \begin{bmatrix} x_H \\ x_V \end{bmatrix} = \begin{bmatrix} \sum_{m=1}^{M} x_H^{PMD}(t_m) \\ \sum_{m=1}^{M} x_V^{PMD}(t_m) \end{bmatrix} \qquad \text{Eq. 17}$$

where M is dependent on the desired length of time of the received data.

Various single-frequency transmissions have been conducted to explore the frequency limits of a polarimetry based vibration transducer. Frequencies from 0.1 Hz up to 25 kHz result in vibration SNR levels>35 dB, suggesting that all frequencies within that entire bandwidth would be easily detectable. The lower limit of 0.1 Hz requires a very long data capture (due to its 10 s period) making it impractical in some applications of the technology, but if computing memory was unlimited, this transducer should operate down to DC. The upper limit of 25 kHz is bounded by the window size and step size of the dynamic PMD analysis as described previously. The chosen step size of 20 us results in a Nyquist frequency of 25 kHz; therefore, vibration signals with frequencies higher than 25 kHz will simply alias back about this axis which will extend the frequency range of application. The minimum detectable signal has also been tested utilizing the example frequency of 100 Hz to find the lower range of detectable vibrational amplitudes.

Figure 15:
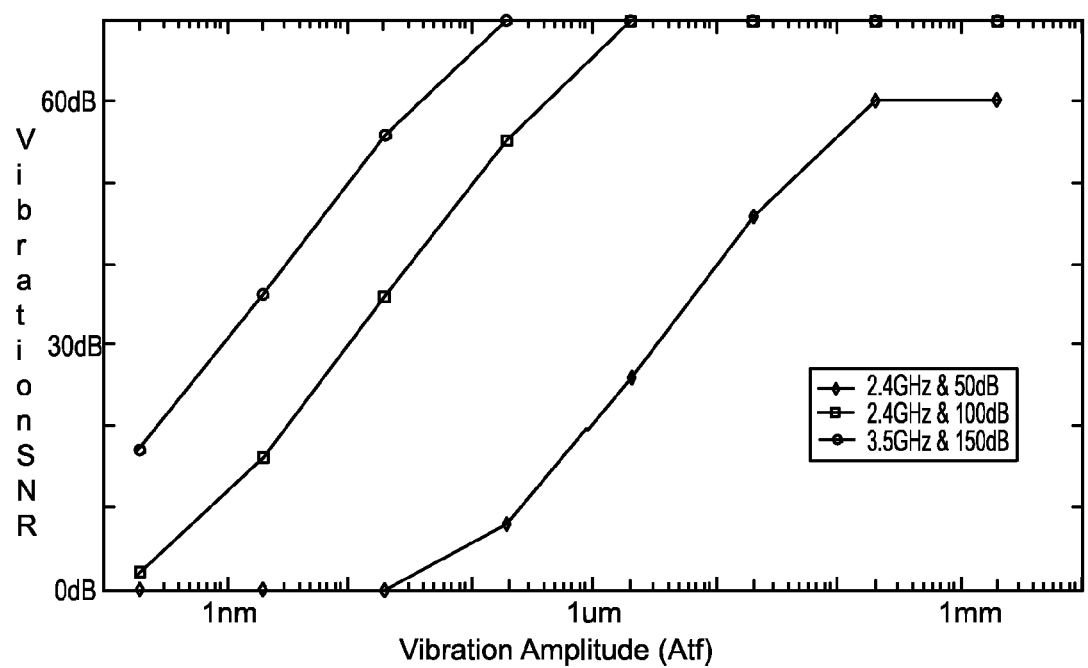
FIG. 15 is an example plot of reflected signal SNRs at different vibration amplitudes for three separate transmissions.

The plot of FIG. 15 contains the SNR levels for three different channel settings. The '2.4 GHz & 50 dB' curve shown in the far right is the nominal parameter settings calibrated to match those described previously, which have a 2.4 GHz Wi-Fi signal with a noise floor 50 dB below. The 26 dB SNR for the 2 um amplitude vibration, which is the amplitude $A_r$, might otherwise be considered the lower end of this particular setup's detectability. But, there are two methods to increase the amplitude range of this transducer. One method is to lower the noise floor. Whereas one particular setup might use unshielded, broad-beam patch-antennas, different equipment combined with more careful channel isolation could substantially lower this 50 dB noise floor, thereby increasing the achievable SNR level. The '2.4 GHz & 100 dB' curve, the middle curve of FIG. 15, simulates the same RF transmit signal with the noise floor lowered from 50 dB to 100 dB below. Now, the 100 Hz signal is clearly detectable (SNR of 16 dB) down to 2 nm. The second method to increase the amplitude range is to increase the frequency of the RF transmit signal. The reduced wavelength of this higher frequency signal will be more sensitive to very small vibrations. Curve '24 GHz & 100 dB', the leftmost curve of FIG. 15, is produced when the RF transmit signal is increased to 24 GHz. This 10× wavelength reduction results in a 10× sensitivity improvement and the 2° A vibration becomes detectable at a 17 dB SNR level. The transmitter-to-object and object-to-receiver distances (dxmit and drvcr, respectively) are important to the operation of a remote vibration sensor and these distances are contained in the time-varying distance which becomes included in the value calculated by Eq 17. Changing these distances in this model has no significant effect on the output results because the propagation channel is not directly modeled or simulated here. It would stand to reason that longer transmit and receive distances would effectively raise the noise floor and lower the signal level, thereby lowering the achievable SNR values. But, that amount of SNR degradation is highly dependent upon the specific channel (i.e., measurement environment) and the transmit/receive hardware chosen. Use of the sensors has confirmed that vibration measurements are not significantly degraded even when the antennas are separated by 3 meters which is the maximum standoff distance specified for many LDV systems.

Detection of Tuning Fork Frequency

Figure 16A:
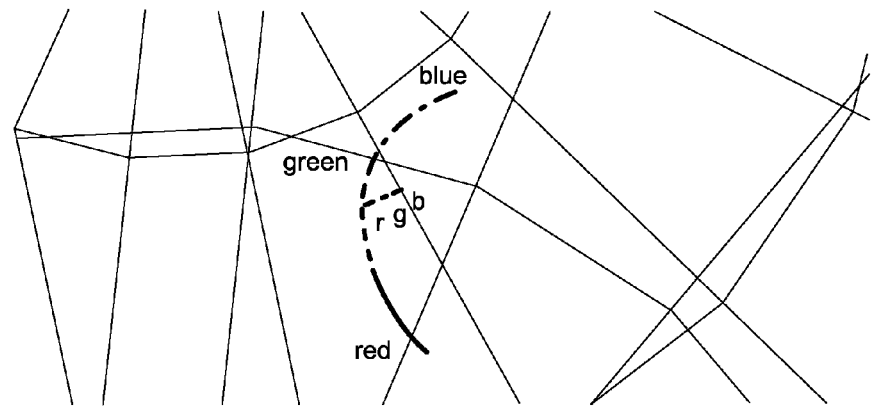
FIG. 16A is an magnified view of an example plot of a PMD response from a tuning fork plotted on a Poincaré sphere.
Figure 16B:
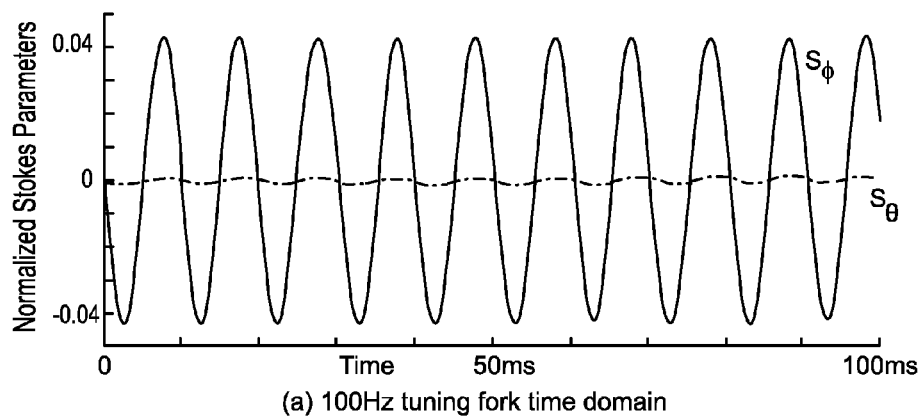
FIG. 16B illustrates an example plot of the time domain and an example plot of the frequency domain of the RF signal reflected from the tuning fork of FIG. 16A.
Figure 16C:
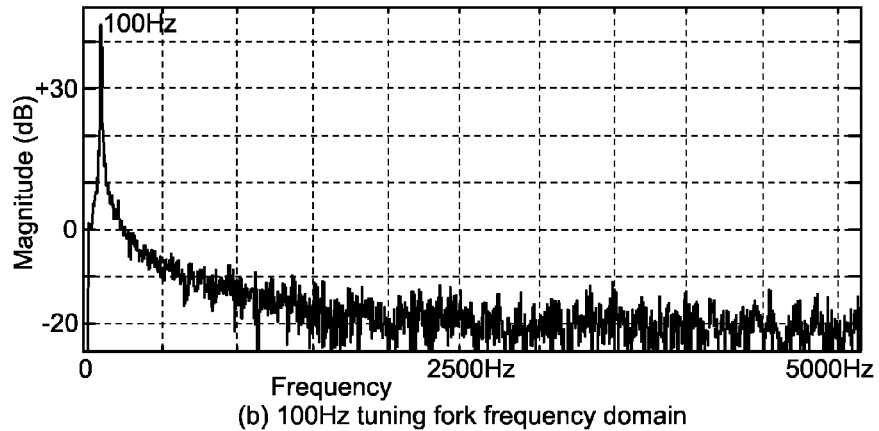
Figure 17:
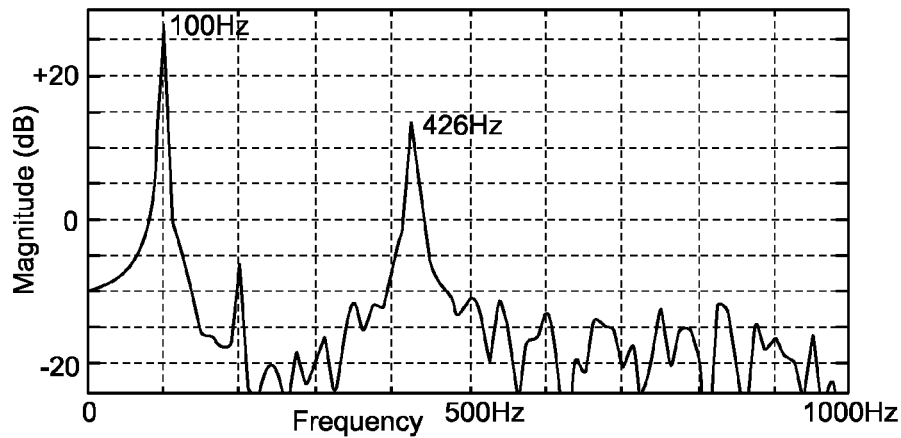
FIG. 17 illustrates an example frequency domain plot.

The vibrations of pure-tone tuning forks were measured to demonstrate this transducer's effectiveness. The 'moving' PMD curve is shown in FIG. 16A and the time-domain and frequency-domain plots of this transducer's output are shown in FIG. 16B for a 100 Hz fork. (Tuning forks of other frequencies, up to 2 kHz, have been tested with similar results.) The 100 Hz vibration of this single tuning fork is clearly visible in all three plots. A second vibrating tuning fork of 426 Hz was added between the antennas and 10 cm from the 100 Hz fork. The narrow beam of an LDV system would require a scanning laser and complicated focusing to measure both of these forks, but the RF polarimetry transducer is capable of sensing this additional vibrator within the propagation channel without any change to the setup. The resulting frequency domain plot of FIG. 17 clearly shows peaks at 100 Hz and 426 Hz. Note, that the 426 Hz signal has a smaller amplitude because its tuning fork is shorter and thicker, thereby limiting the displacement of its vibrating prongs compared to the 100 Hz fork.

Detection of Telephone Ringer

Figure 18:
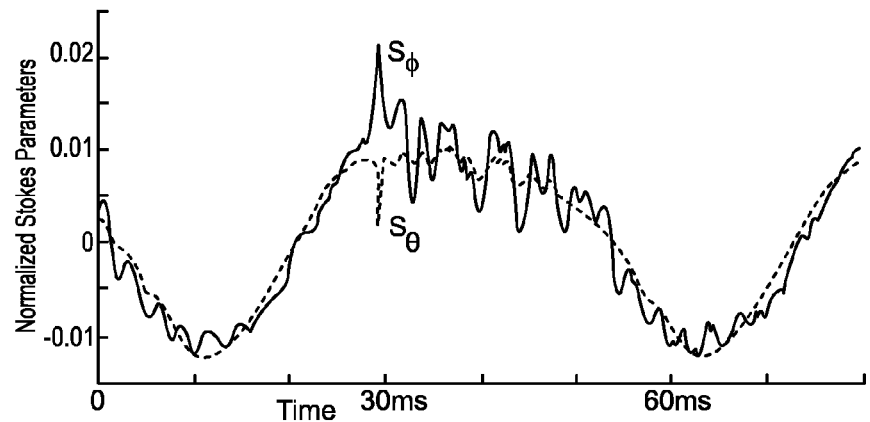
FIG. 18 illustrates an example time domain plot.
Figure 19:
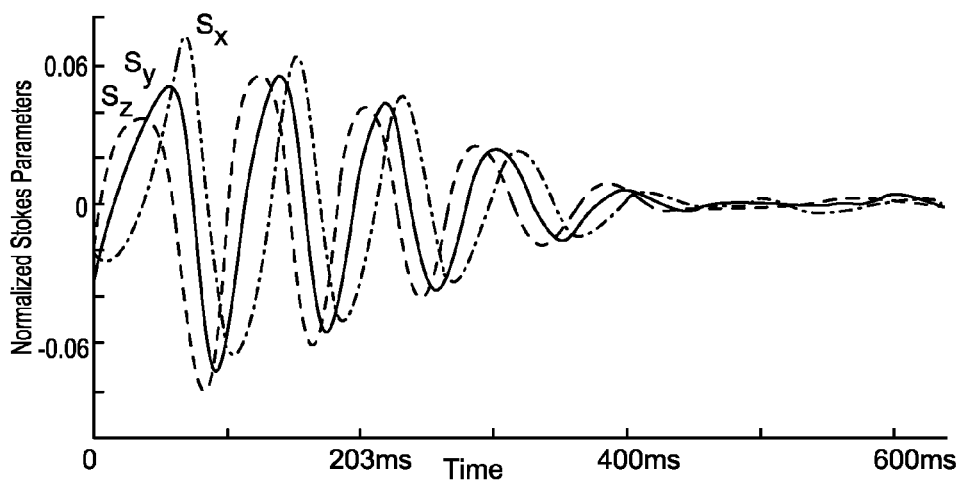
FIG. 19 is an example plot of a time domain plot of the calculated Cartesian Stokes parameters from a dampened, free vibration of a plate.

The ringing of a telephone was measured with RF polarimetry transducer of the type disclosed herein. Phones popular in the 20$^{th}$ century were made to ring as follows: a 20 Hz square wave is used to excite an electromagnet; a steel ball within the field of that electromagnet is propelled back-and-forth at 20 Hz; two large bells (or gongs) are located at each end of the steel ball's path; the ball collides with the bells to ring the phone. In the measurement that was made and described below, one of the two bells was disabled to more clearly show the ringing signal. Importantly, this RF measurement was captured through the plastic housing of the telephone. An LDV system would be unable to measure through any opaque surface. The time domain plot of FIG. 18 clearly shows the forced vibration of the 20 Hz excited steel ball and the higher frequency free vibration of the ringing bell, starting near the 30 ms point in time. The free vibration is transient and is fully damped in about 40 ms—just before the next impact of the (20 Hz) 50 ms periodic steel ball.

Detection of Free, Damped Vibration

A simpler experiment demonstrating another damped, free vibration response is taken on a 20"×30" metal plate supported by one of its sides. The plate is impacted with a wooden mallet, and the time-domain vibrational response is shown in FIG. 12. This continuous system measurement illustrates the vibrational amplitude decrease associated with a damped system.

Detection of Rotational Machinery

Figure 20A:
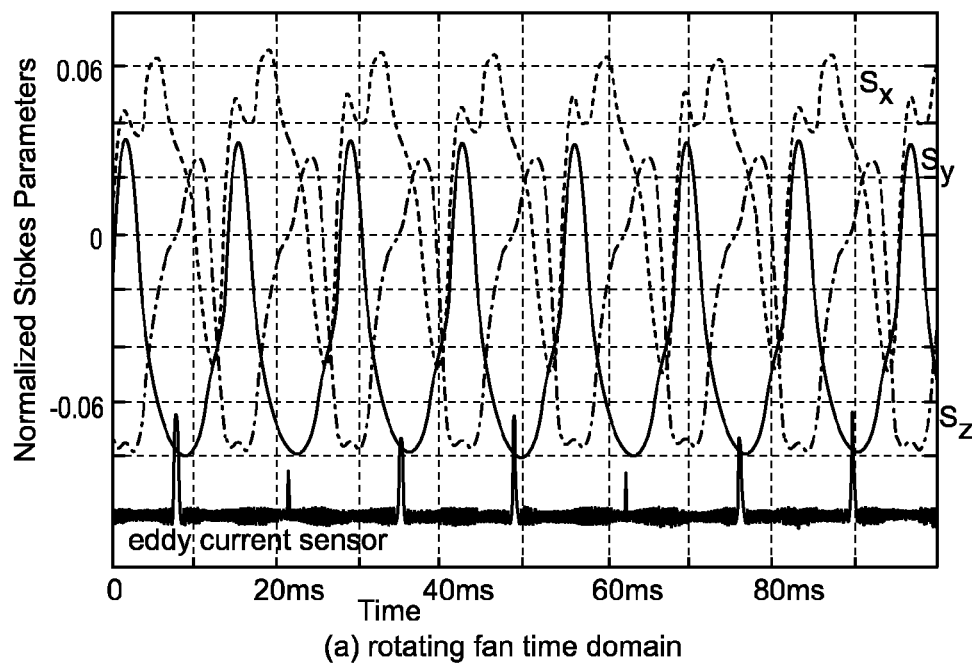
FIG. 20 is an example plot of a time domain and frequency domain plots of the RF signal reflected from a common 3-bladed fan.
Figure 20B:
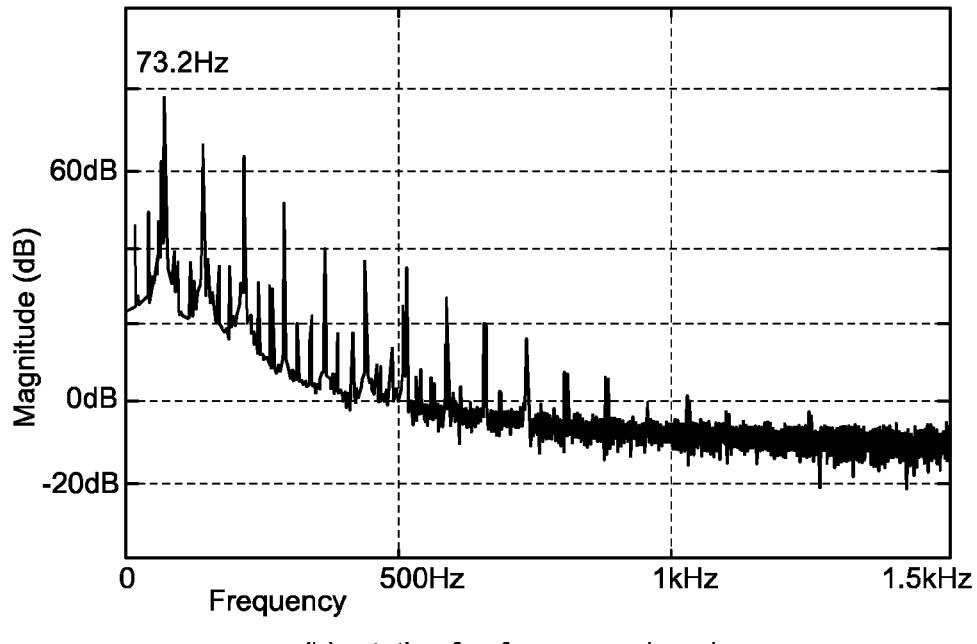

Rotating machines exhibit near-periodic motions as they turn throughout 360 degrees. This regular motion can be transformed from the mechanical rotation into a near-periodic, temporal, electrical signal via one or more transducers. The machine's rotational motion translates into periodic motions and vibrations of its various rotating parts (shafts, bearings, gears, rotors, etc.). This temporal data can be collected and processed in order to access the 'health' of a rotating machine. Particular failure modes will manifest themselves in the time-domain and frequency-domain responses of this data. For example, an out of alignment fan blade, or vane, may produce an unbalance that amplifies one or more harmonics of the fundamental rotational speed. Or, a bearing defect may result in one or more spurious frequency components at non-harmonics of the rotational speed. Data processing techniques can be used to separate these failure modes, whether for characterization, diagnostic, or prognostic purposes. The vibration transducer was used to monitor the rotation of a common desk fan having three metal fan blades. Two antennas are positioned about a few meters on either side of the common desktop fan. The time domain and frequency domain plots are shown in FIG. 20. The signal from an eddy-current proximity probe positioned near the tip of the fan blades is also plotted on this same time-domain graph. The upward spikes in its signal correspond to each fan blade passing near the proximity probe during rotation—three spikes for one rotation, due to the three fan blades. This second sensor provides an accurate confirmation of the rotation frequency measured by the RF Polarimetry sensor. The fundamental frequency appears to be near 73 Hz, but the true rotational speed of the fan is one-third that rate, or 1463 rpm. The three nearly-identical fan blades create this 3× speed up effect. Additional PMD signature analysis (as discussed in Section V) could discriminate between each of the three, nearly-identical fan blades.

Figure 21:
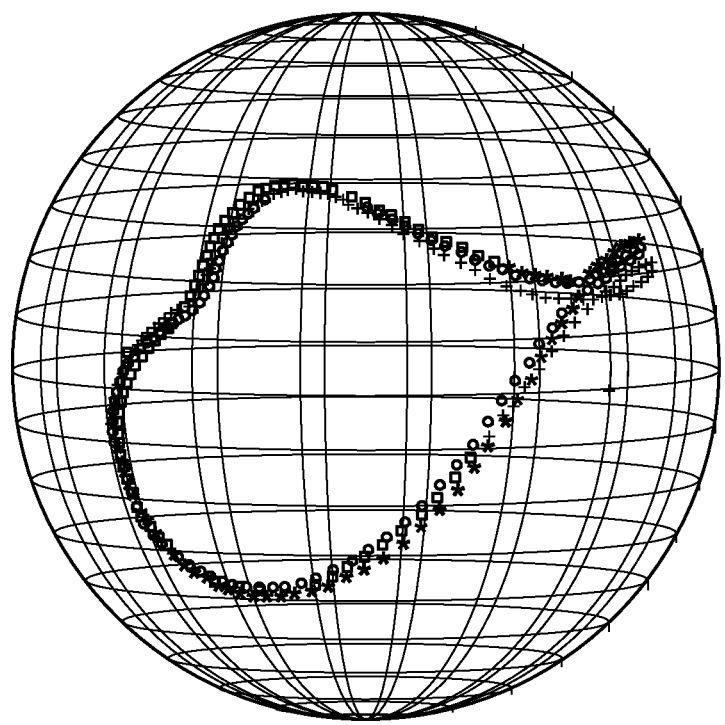
FIG. 21 is an example plot of a data of FIG. 20 as plotted on a Poincaré sphere.
Figure 22A:
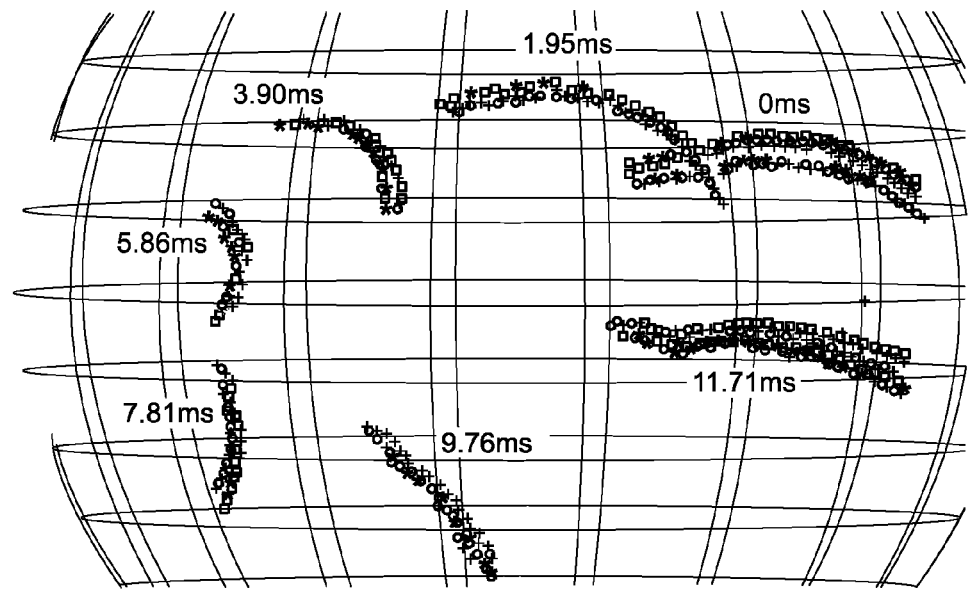
FIGS. 22A and 22B together illustrate an example full, temporal curve plotted on a Poincaré sphere.
Figure 22B:
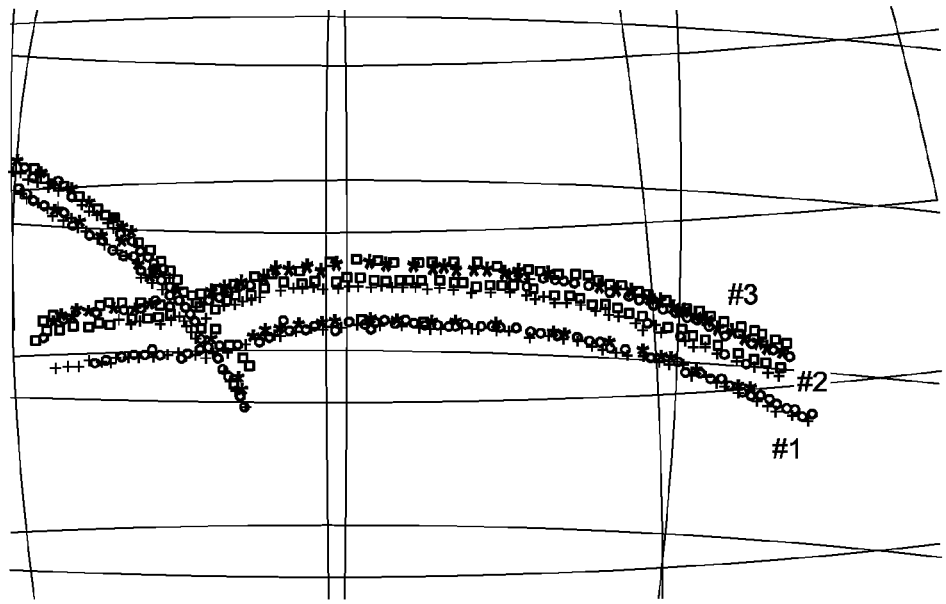
Figure 23A:
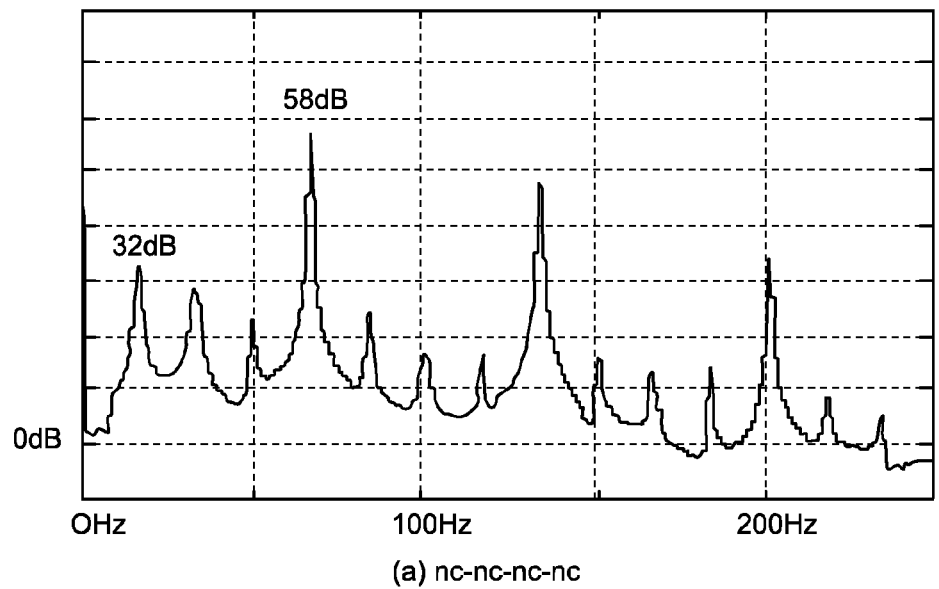
FIG. 23A-23D together illustrate an example plot of a frequency domain for a healthy fan, and for a modified fan illustrating at least one blade defect.
Figure 23B:
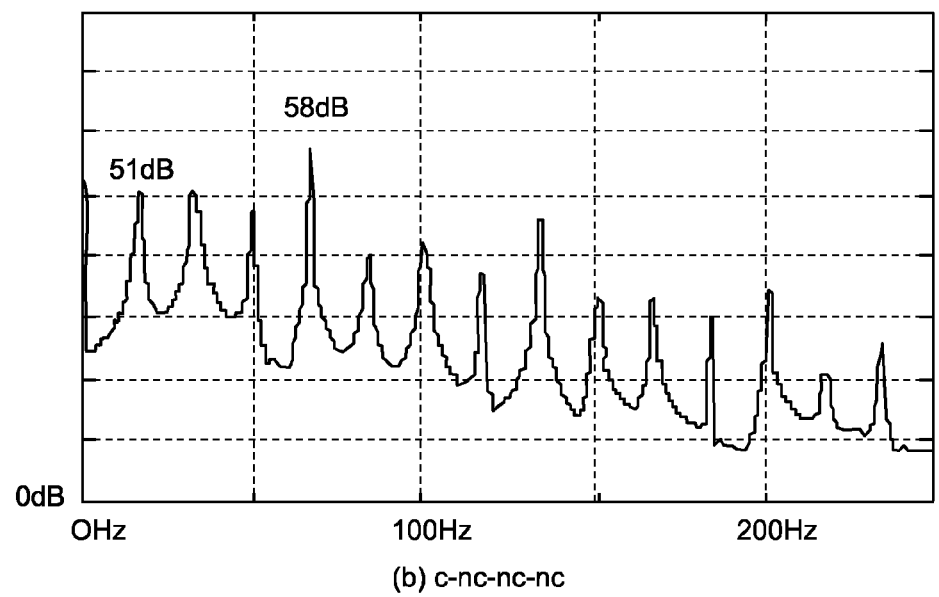
Figure 23C:
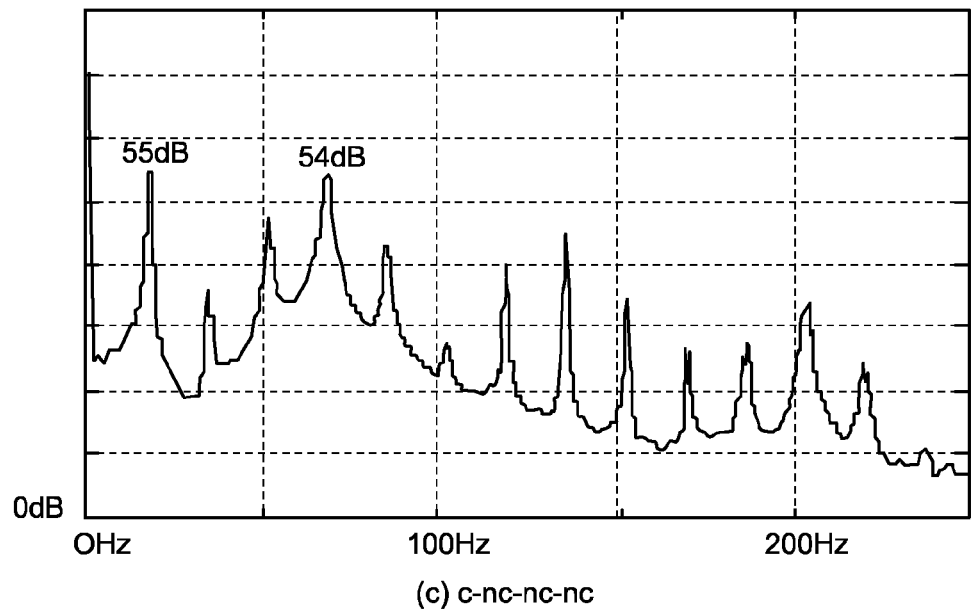
Figure 23D:
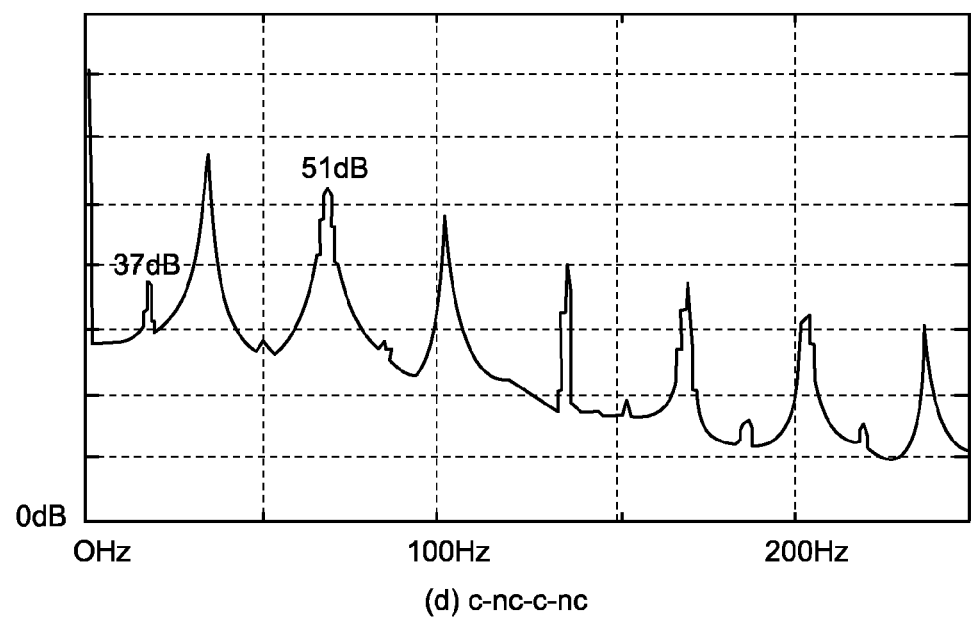

Polarimetric data can be used in subsequent processing to analyze the rotating machinery in two ways. First, the average, or centroid, of the time-varying PMD responses is analyzed in both the time-domain and the frequency-domain. The 3-dimensional, temporal Stokes centroid data of FIG. 20 be plotted on the Poincaré sphere as in FIG. 21. One complete shaft revolution (41.0 ms) is plotted (colored from blue-to-green-to-yellow-to-red in time), which results in three nearly identical loops across the sphere due to the three nearly identical fan blades. Each dot on this plot represents the centroid (or average) of the time-varying PMD responses. Second, the complete PMD responses are analyzed temporally on the Poincaré sphere. The unique location and shape of each PMD response corresponds to a particular rotational orientation of the fan blade. A measured change in one or more of the sub-carrier frequencies would indicate a deviation from the rotating machine's expected periodic motion. By tracking multiple sub-carriers across a wide bandwidth, a greater sensitivity and a higher level of defect identification is possible, versus the averaged, centroid approach. As described previously, the full PMD curve, Sv(t; k), can be calculated covering each sub-carrier, k, of the RF signal's full bandwidth over time. These full, temporal curves can then be plotted on the Poincaré sphere, as in FIG. 22. Here, the temporal PMD response data is sampled at a slower rate (seven equal division per vane-pass period or 21 equal divisions per shaft period) than the centroids of FIG. 21, due to the larger sizes of these full curves. The full PMD responses for three complete shaft revolutions are plotted. Consequently, each of the 7 groupings of PMD curves contains a total of 9 similar curves. The groupings are labeled according to their time location for the first vane-pass period (0 ms, 1.95 ms, 3.90 ms, . . . ). For the second vane-pass period they would be offset by 13.7 ms (13.7 ms, 15.95 ms, 17.6 ms, . . . ), and so on. Note that the response exhibits a periodicity that is related to the number of blades in the fan. In this case, the fan has three blades that are similar, but are not exactly aligned. A rotation of either 120 degrees or 240 degrees yields a similar, but not identical response to the one at 0 degrees. Only a full 360-degree rotation gives an identical response. Hence, the PMD response at 0 degrees, 120 degrees, and 240 degrees are all slightly different, but the responses repeat once the blade has rotated through a complete revolution of 360 degrees. For clarity, a zoom-in of the grouping labeled "0 ms" is provided in FIG. 22B. Two observations are clear from this figure. First, each vane-pass period produces a unique PMD response—this 3 blade fan produces three unique PMD curves labeled "#1, #2, and #3" due to slight differences in each blade. Second, each shaft period produces a PMD curve that precisely overlays the pervious one—there are three superimposed curves at each of the "#1, #2, and #3" locations.

These two observations lead to two valuable conclusions: 1.) Even though the 3 blades of the fan appear very similar, they are in fact measurably different. If the design goal calls for three identical fan blades, then this full PMD response data could be used to make the necessary adjustments (i.e. to perfectly align all nine of these periodic PMD curves). 2.) The rotating speed and overall 'health condition' of this fan is very consistent over the three shaft periods (123 ms) plotted here. By continually monitoring these full PMD responses, any slight change in the curves' shapes or locations could be used as an indicator, or even a future predictor, of a defect, fault, or failure of the rotating machine. Rotating machine analysis could be performed by operating on any one of the three time-domain Stokes parameter sequences from FIG. 20. A simple FFT of this temporal PMD centroid time-domain sequence could then be plotted in the frequency-domain. Or, a joint detection approach can be employed that involves squaring and summing the spectral responses of each Stokes sequence (S1, S2, and S3). Application of this square-sum approach to the temporal PMD centroid fan blade data yields the results presented in FIG. 20. It is seen that the dominant spectral peak formed from an FFT of the joint Stokes parameters provides an estimate of a rotational rate that is scaled by the number of fan blades.

The plots of FIG. 23 demonstrate such capability where an otherwise 'healthy' fan has been modified to create defects or faults for analysis using this RF polarimetry technique. For these measurements, a 4 bladed fan was purposely modified to detect potential equipment failure modes. The 'defects' or 'faults' were created by attaching small metal clips (1.5 inches long) to various fan blades. These attached metal clips will create two effects on the measured signals: 1.) They will alter the reflection and scattering of the RF signals. As such, they will simulate a physical defect (such as a crack or fracture) or a change (maybe a bend or deflection) in the corresponding fan blade. 2.) They will unbalance the fan's rotation due to their added weight and air drag. As such, they will mimic a defect in the shaft, bearings, or other rotating components that could result in unbalanced conditions. The 4 bladed fan allows for several variations of failure modes—one blade clipped, two adjacent blades clipped, and two non-adjacent blades clipped will be used here. The frequency domain plots for a healthy fan (no clips) and those three failure mode variations are provided in FIG. 23. The status of the 4 blades is given under each plot with "nc" representing 'no clip' and "c" representing 'clip'. It is clear that the spectral components of the healthy fan, FIG. 23A with no blades clip which represents a sort of baseline to the other plots, are significantly altered by the addition of the clips, FIGS. 23B, C, and D. Furthermore, the distinctive 'signatures' of these faulty machine frequency responses provides an insight into the particular failure modes or defects For example, the increase of the fundamental relative to the fourth harmonic (the vane-pass frequency) in FIG. 23B suggests an out of balance rotation caused by the single clip. The greater increase of the fundamental relative to the second and fourth harmonics in FIG. 23C suggests a greater odd mode unbalance caused by the two adjacent clips. While the dominance of the even harmonics in FIG. 23D suggests an even-mode failure caused by the alternating clip no-clip pattern.

The examples provided above exploit the RF polarimetric transducer's ease of setup (roughly positioning two antennas) and aggregate sensing (detection multiple vibrating element in a given field), and penetrating sensing capability (detecting vibrating elements even behind plastic). These advantages are made possible by utilizing an electromagnetic wave in the radio frequency region—as opposed to LDV systems which uses an optical path and subject to the limitations of such an object. But, these unique properties of RF signals should be considered when implementing this transducer. It should be noted that if the RF properties of the specific bands mentioned hereto are undesirable for a particular application, a different transmitted frequency can be employed, such as in the MHz, GHz, or THz range. The PMD analysis of such a system would remain largely the same as has already been taught herein.

It should be noted that any movement by a detectable object within the RF propagation channel will affect the received RF signal's polarization. For instance, seismic vibrations that often faintly shake a building, floors, and walls will be sensed by the RF signals which reflect off of those surfaces; whereas, other systems might only pickup the seismic vibrations that shake the object under test. With proper selection, placement, and shielding of both the transmit and receive antennas, the received SNR of these seismic noises can be greatly reduced relative to the vibrational range of interest. Furthermore, since these seismic vibrations are typically at lower frequencies, high-pass filtering of the vibrational data can be used to effectively remove them from the analysis. As demonstrated with the two tuning forks and the ringing telephone experiments, the aggregate sensing field of RF is useful for detecting multiple vibrators; whereas, an LDV system would require an additional laser or a scanning capability. However, these aggregate signals can only be separated by their differences in frequency. Band-pass filtering of the vibrational data could precisely extract many different frequencies (e.g. the six tones of a strummed guitar can be easily measured).

Figure 24:
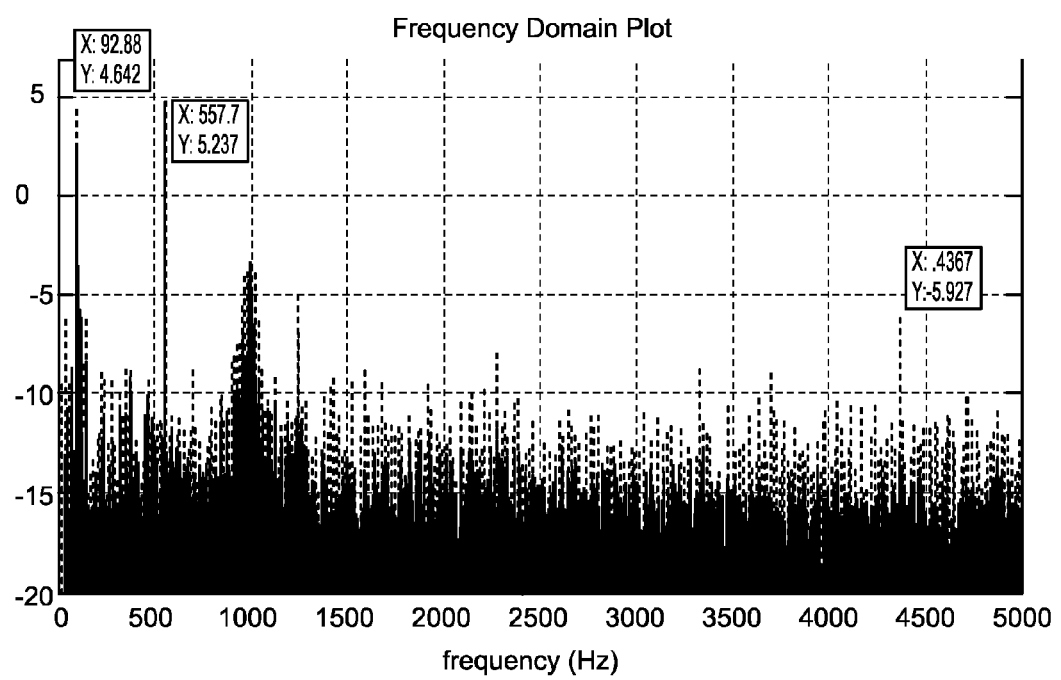
FIG. 24 illustrates an example detection of a strain in accordance with the teachings of the present disclosure.

In another example, the system 200 can be used in place of a strain gauge to produce the results displayed in FIG. 24. A material or structure undergoing strain will have some physical deformation which can be sensed based on electromagnetic, or radio frequency, signals reflect, scatter, or are otherwise transmitted through a body under strain.

Figure 25A:
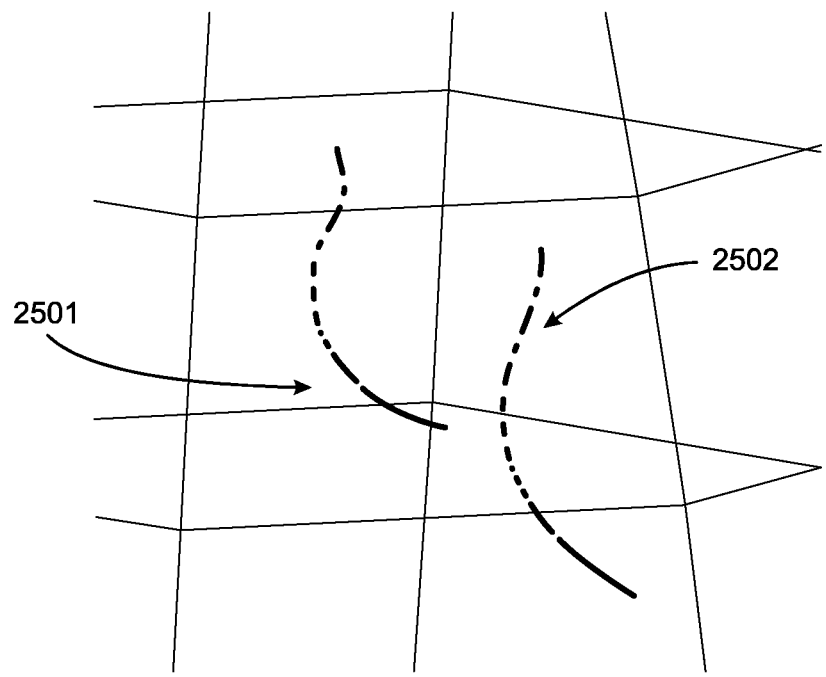
FIG. 25A illustrates an example detection of cavitation as plotted on a Poincaré sphere.
Figure 25B:
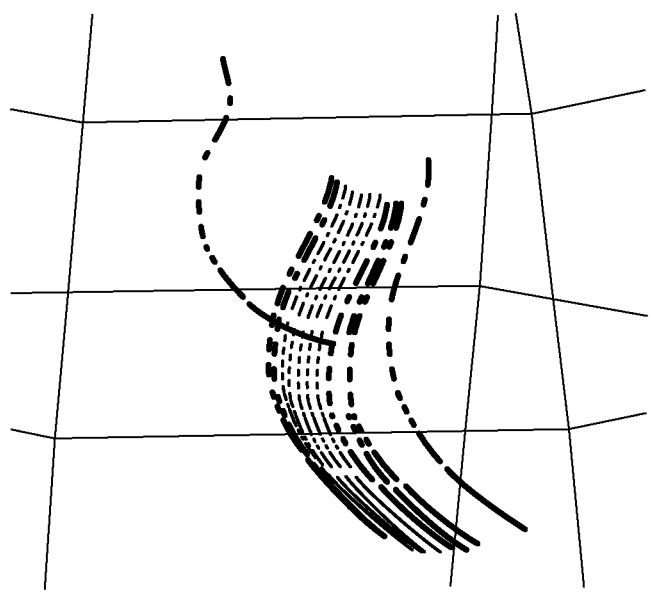
FIG. 25B illustrates an example detection of a time-series of data for system undergoing various degrees of cavitation as plotted on a Poincaré sphere.
Figure 26:
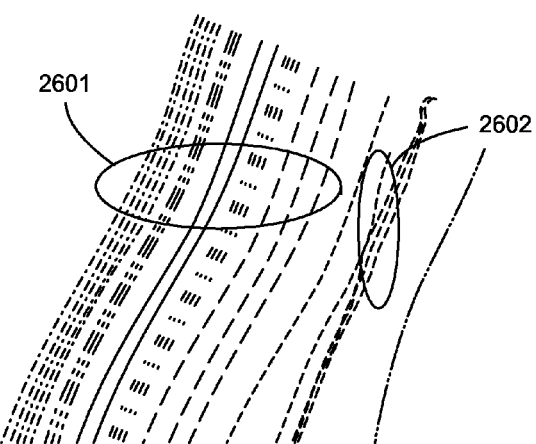
FIG. 26 illustrates a detailed view of the Poincaré sphere of FIG. 25.
Figure 27:
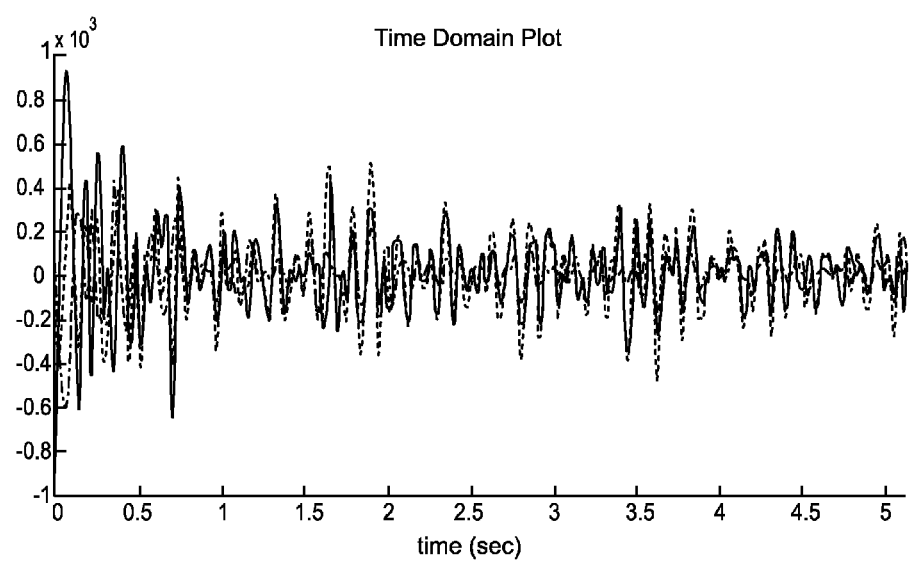
FIG. 27 illustrates an example detection of cavitation by plotting a time domain plot of calculated Stokes parameters.
Figure 28:
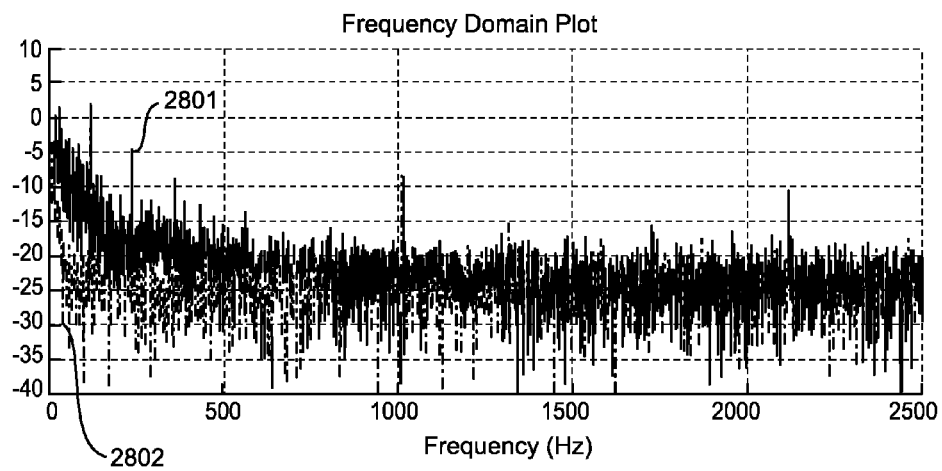
FIG. 28 illustrates the frequency domain plot of the data of FIG. 27.

The system 200 may be employed to discriminate a change or difference in flow conditions of a fluid. For example, in one embodiment, a fluid flow may have more than on phase present. In such instances, the received PMD signature of such a flow would be distinguishably different. The void fraction present in such a fluid flow has a directly correlated effect the polarization of a transmitted wave such that in some instances it will be possible to calculate the amount of void fraction present. Systems with 2502 and without cavitation 2501 may be easy to differentiate when their PMD response is plotted in the Poincaré sphere as can be seen in FIG. 25A as these two curves plot on different parts of the sphere. As a system experiences varying levels of cavitation between a severe state (typically one with more void fraction per given area) and a less sever state (typically one with less void fraction per given area), the PMD response as can be seen to move along the Poincaré sphere, such as for example, as seen in FIG. 25B. In FIG. 25B, the PMD response for a system under cavitation can be seen on the right of the plot. This plotted received response then moves to the left of the plot towards a position where the PMD response where a cavitation-free system would plot as the system is transitioned to less severe cavitation and lower void fraction. The detected PMD response for a known cavitation condition could be correlated to the received response from the same system, which may need to account for any other environmental factors that may affect the received electromagnetic multipath. However, these are not the only differences that are distinguishable by sensing a polarimetric response to a reflected wave. The shape of the PMD curve is also a distinguishable characteristic for cavitation detection. Reviewing FIG. 26, it can be seen that in systems without the presence of cavitation there is a slight bend 2601 in the PMD curve as opposed to systems with cavitation where there is no bend 2602. Still further, in some instances it is possible to detect cavitation by the time domain plot of the calculated Stokes parameters as seen in FIG. 27. Cavitation is detectable by the amount of signal received where, according to the system depicted by FIG. 27, cavitation is present at time 0 and then the system transition a cavitation-free environment around 2 seconds at the amplitude of the plotted parameters subsided. The frequency domain plot, as presented in FIG. 28 shows systems in cavitation 2801 with higher amplitude of low frequency signals than those without cavitation 2802.

Figure 29:
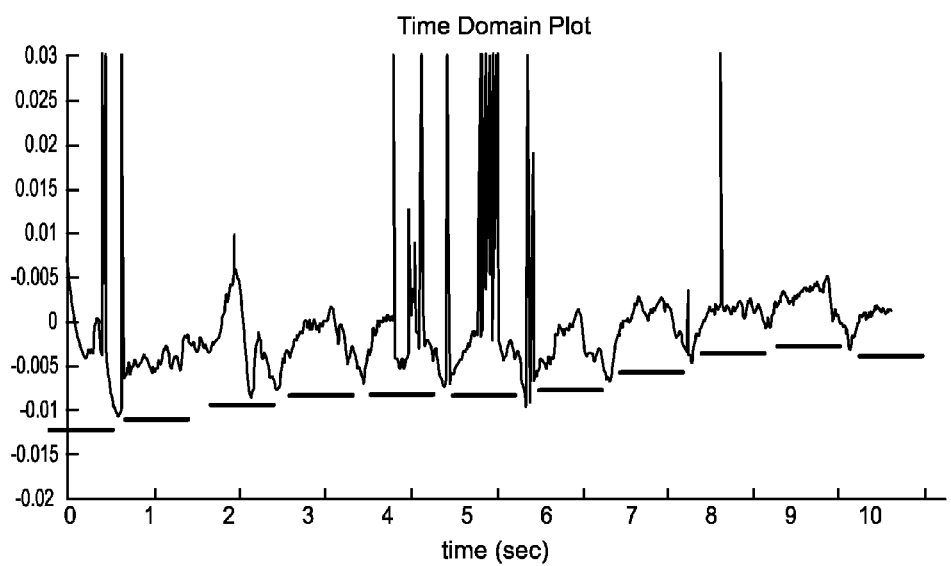
FIG. 29 illustrates a time domain plot of a detection of an example heartbeat.

In still additional examples, the system 200 may be configured for medical purposes, including biometric measurements. In one instance, the example system 200 may be specifically used as a thoracic biometric heart monitor. In this occasion, the RF polarimetry is used to characterize for identification and monitoring by scattered, polarized RF signatures from the heat during respiration, and/or contraction and relaxation of the heart muscle. In this way a non-invasive biometric measurement may be obtained. As shown in the time domain plot of FIG. 29, a heartbeat may be sensed by the regular pulses of sensed reflected RF energy. The data displayed in this plot may be improved through the used of filtering as well as signal and equipment optimization to improve the displayed data.

Figure 30:
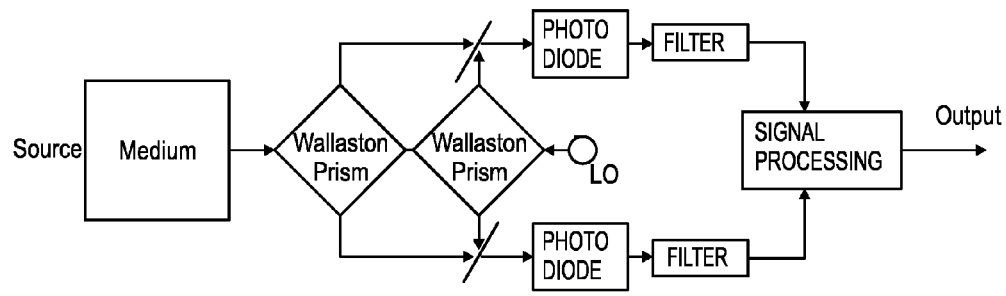
FIG. 30 illustrates an example system for employing higher frequency detection and PMD characterization.

Received PMD signals may also be used to interrogate biomaterials such as tissues, organs, cells, or fluids. These materials can be tested with the system 200 in order to determine their state to include possible affliction with a disease. In one embodiment, one may detect a tumor or cancerous cell or group of cells by their PMD signal (i.e. received polarization information after reflecting a transmitted signal). In some embodiments it may be necessary to use higher frequency wavelengths such as THz or even visible or near-visible light wavelengths. Depicted in FIG. 30 is an example system that could employ such higher frequencies and permit the same PMD characterization as is otherwise described herein. What's more, the present system 200 may be utilized to for interference suppression, such as in power line communications, wireless communication and radar, astronomy, other sensor systems, etc. In addition, the system 200, may be utilized for noise quality characterization based, communications with modulated polarization as an overlay.

The system 200 may also be used as a sensor for the electronic signal environment. It may be used in electronic warfare applications such as electronic protection or electronic attach. Similarly, such a system 200 can be used in for indication, surveillance, and recognizance (ISR). The PMD characteristic of received signals can be characterized as to provide information about how a transmitting signal is operating.

Still further, we anticipate that a "PMD Analyzer", akin to a spectrum analyzer, could be manufactured to measure, analyze, and display PMD measurements and related data products in approximate real time. The analyzer would have two or more RF inputs (or equivalently IF inputs or I/Q pairs). It would have capability to control the way in which the received signals are conditioned and the way in which the digitized inputs signal samples are processed to obtain PMD estimates and other measurements derived from the PMD estimates. Further, it would have capability to control the display of the PMD and related metrics. It would also have a capability for the user to define signal processing algorithms on the backend to process the PMD measurements to generate outputs defined by the user, and for these custom outputs to be displayed.

Finally, the example system 200 may be utilized as a cyber-security device. In this case, multiple modes occur in wireless, fiber optic, and power line conductors, and unique and/or distinguishable signatures may occur for each link. The system 200 can thus exploit this phenomenon to discriminate true networks clients in these electromagnetic media if the receivers at each demodulator retransmit point within a network carry the signal forward.

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents.

We claim:

1. A method of identifying changes utilizing polarization comprising:
   receiving polarized and coherent components of an at least partially polarized multipath signal at a receiver, wherein at least one signal path of the multipath signal is at least one of reflected off of a surface of a target object or transmitted through the target object;
   computing the Stokes parameter versus the frequency index of the subcarrier present within the received signal;
   calculating polarization as a function of frequency to determine the polarization mode dispersion of the received multipath signal;
   detecting a change in a polarization mode dispersion in response to a change in the target object; and
   displaying on a user interface the detected change in the polarization mode dispersion as a digital representation of the change in the target object.

2. A method as defined in claim 1, wherein detecting a change in the polarization mode dispersion in response to a change in the target object further comprises comparing the polarization features of the processed signal to a known calibration.

3. A method as defined in claim 2, wherein the known calibration is a predictive model and wherein comparing the polarization features of the processed signal to the known calibration allows for prediction of an impending change in the target object.

4. A method as defined in claim 2, wherein the known calibration is determined by measuring a polarization signature of the processed signal and comparing the measured polarization signature to a known standard measurement.

5. A method as defined in claim 1, wherein detecting a change in the polarization mode dispersion in response to a change in the target object further comprises comparing a polarization mode dispersion feature of the processed signal to a previously elicited polarization mode dispersion feature of the received signal.

6. A method as defined in claim 1, wherein detecting a change in the polarization response of the target object is indicative of a change in a characteristic of the target object comprising at least one of vibration, attitude change, mechanical fault, structural change, or foreign object contamination of the target object.

7. A method as defined in claim 1, wherein an elicited polarization feature in a first subband of the received signal is compared against an elicited polarization feature of the received signal in a second subband.

8. A method as defined in claim 1, wherein the elicited polarization feature is a polarimetric mode dispersion of at least one subband of the received signal.

9. A method as defined in claim 1, wherein detecting a change in the polarization response of the target object is indicative of a change in a characteristic of the target object comprising at least one of electrical fault, electromagnetism, reflectivity, liquid phase, or solid phase.

10. A system for identifying changes utilizing polarization comprising:
    a polarized receiver for receiving polarized and coherent components of a polarized multipath signal at a receiver, wherein at least one signal path of the multipath signal is at least one of reflected off of a surface of a target object or transmitted through the target object;
    a signal filter for filtering the received signal;
    a signal amplifier for amplifying the received signal;
    a signal conditioner for conditioning the received signal;
    an analog to digital converter for converting the signal from an analog format to a digital format;
    a processor for computing the Stokes parameter versus the frequency index of the subcarrier present within the received signal and calculating a polarization mode dispersion feature of the received signal,
    wherein the processor detects a change in the polarization mode dispersion signature of the target object; and
    a display for displaying on a user interface the detected change in the polarization mode dispersion signature of the target object.

11. A system as defined in claim 10, wherein the processor detects a change in a characteristic of the polarization mode dispersion signature of the target object by comparing the detected polarization mode dispersion signature of the dispersion signature to a known calibration stored in a memory.

12. A system as defined in claim 11, wherein the known calibration is determined by measuring the polarization mode dispersion signature of the target object and comparing the measured polarization mode dispersion signature to a known standard measurement.

13. A system as defined in claim 10, wherein detection of the change in the polarization mode dispersion signature of the target object is indicative of a change in a characteristic of the target object comprising at least one of vibration, attitude change, mechanical fault, structural change, or foreign object contamination of the target object.

* * * * *